United States Patent [19]

Miller et al.

[11] Patent Number: 5,198,347
[45] Date of Patent: Mar. 30, 1993

[54] DNA ENCODING *PLASMODIUM VIVAX* AND *PLASMODIUM KNOWLESI* DUFFY RECEPTOR

[75] Inventors: Louis H. Miller; John H. Adams, both of Bethesda; David C. Kaslow, Kensington; Xiangdong Fang, Bethesda, all of Md.

[73] Assignee: The United States of America as represented by the Department of Health and Human Services, Washington, D.C.

[21] Appl. No.: 554,837

[22] Filed: Jul. 20, 1990

[51] Int. Cl.[5] .................. C12N 15/12; C12N 15/63
[52] U.S. Cl. .......................... 435/69.1; 435/257.3; 435/320.1; 530/350; 536/23.7
[58] Field of Search ............... 435/69.1, 252.3, 320.1; 530/350; 536/27

[56] References Cited

PUBLICATIONS

J. Mol. Biol, 203:707-714, 1988, Hudson et al. Molecular Basis for Mutation in a Surface Protein Expressed by Malarial Parasites.
Nucl. Acid Res. 11:7119-7136, Oct. 1983, Breathnach et al. Plasmids for the cloning and expression of full-length double-standard CDNAS under control of the SV40 early or late . . . .
Miller et al., Science 189: 561-563, 1975.
Miller et al., N. Engl. J. Med. 295: 302-304, 1976.
Miller et al., J. Exp. Med. 149: 172-184, 1979.
Haynes et al., J. Exp. Med. 167: 1863-1881, 1988.
Miller et al., Mol. Biochem. Parasitol. 31: 217-222, 1988.
Wertheimer et al., Exp. Parasitol 69, 340-350, 1989.
Barnwell et al., J. Exp. Med. 168: 1795-1802, 1989.
Denise Mattei, et al., reactive antigenic determinants present on different *Plasmodium falciparum* blood-stage antigens, Parasite Immunology 1989, 11, pp. 15-29.
Peera Buranakitjaroen and Christopher I. Newbold, Antigenic cross reactivity between p195 and a distinct protein of 100 kDa in *Plasmodium falciparum*. Molecular and Biochemical Parasitology, 22, (1987) pp. 65-77.
David C. Kaslow et al., A vaccine candidate from the sexual stage of human maleria that contains EGF-like domains, vol. 333, No. 6168 pp. 74-76 May 5, 1988.
A. Saul, et al., Cross-reactivity of antibody against an epitope of the *Plasmodium falciparum* second merozoite surface antigen, Parasite Immunology 1989, 11, 593-601.
Nirbhay Kumar et al., *Plasmodium falciparum* gene encoding a protein similar on the 78-kDa rat glucose-regulated stress protein, vol. 85, pp. 6277-6281, Sep. 1988.
Mats Wahlgren et al., A *Plasmodium falciparum* antigen containing clusters of asparagine residues, vol. 83, pp. 2677-2681, Apr. 1986.

*Primary Examiner*—David L. Lacey
*Assistant Examiner*—John D. Ulm
*Attorney, Agent, or Firm*—Cushman, Darby & Cushman

[57] ABSTRACT

The present invention relates to DNA segments encoding the Duffy receptor of a Plasmodium parasite, the recombinant DNA and to recombinantly produced Duffy receptor. The Duffy receptor can be utilized as a vaccine for humans against malaria.

10 Claims, 30 Drawing Sheets

```
                                                          oligo 30
AATTCTGTAAGGATATAAGATGGGGGTTGGGGGATTTTGGAGACATAATTATGGGAACTAATATG
 F  C  K  D  I  R  W  G  L  G  D  F  G  D  I  I  M  G  T  N  M  E
                                                DR.2 starts  |——>
GAAGGTATTGGGTATTCCCAAGTAGTGGAAAATAATTTGCGCCAAGTCTTTGGAA          120
 G  I  G  Y  S  Q  V  V  E  N  N  L  R  Q  V  F  G              39
      oligo 13
CTGATGAAAAGGCCAAGCAGGATCGTAAACAATGGTGGAATGAATCTAAGGAACATATATGGAGA
 T  D  E  K  A  K  Q  D  R  K  Q  W  W  N  E  S  K  E  H  I  W  R
GCAATGATGTTCTCAATTAGGAGCAGATTAAAGGAGAAATTTGTGGATTTGTA           240
 A  M  M  F  S  I  R  S  R  L  K  E  K  F  V  W  I  C            79

AAAAGATGTTACGTTAAAAGTAGAACCCCAGATATACAGGAGGATTCGAGAATGGGGAAGAGAT
 K  K  D  V  T  L  K  V  E  *  Q  I  Y  R  W  I  R  E  W  G  R  D
TATATGTCAAAATTACCCAAAGAACAGGGGAAACTAAATGAAAATGTGCTAGTA         360
 Y  M  S  K  L  *  K  E  Q  G  K  L  N  E  K  C  A  S           119

AATTATACTATAATAATATGGCAATATGTATGTTGCCTCTGTGCCATGATGCCTGTAAATCATAT
 K  L  Y  Y  N  N  M  A  I  C  M  L  P  L  C  H  D  A  C  K  S  Y
GATCAATGGATAACAAGGAAAAAACAATGGGATGTTTTGTCAACAAAATTTT           480
 D  Q  W  I  T  R  K  K  Q  W  D  V  L  S  T  K  F               159

CAAGTGTAAAGAAGACACAAAAAATCGGGACGGAAAATATCGCAACAGCTTATGATATACTAAAA
 S  S  V  K  K  T  Q  K  I  G  T  E  N  I  A  T  A  Y  D  I  L  K
CAGGAATTAAATGGATTTAAAGAGGCGACTTTTGAGAATGAAATTAACAAACGTG         600
 Q  E  L  N  G  F  K  E  A  T  F  E  N  E  I  N  K  R           199
```

FIG. 1A

```
                                                              oligo 30
AATTCTGTAAGGATATAAGATGGGGGTTGGGGATTTTGGAGACATAATAATGGAACTAATATG    120
 F  C  K  D  I  R  W  G  L  G  D  F  G  D  I  I  M  G  T  N  M  E   39
                                        DR.2 starts |——>
GAAGGTATTGGGTATTCCCAAGTAGTGGAAATAATTGCGCCAAGTCTTTGAA              
 G  I  G  Y  S  Q  V  V  E  N  N  L  R  Q  V  F  G                
    oligo 13
CTGATGAAAAGGCCAAGCAGGATCGTAAACAATGGTGGAATGAATCTAAGGAACATATATGGAGA  240
 L  D  E  K  A  K  Q  D  R  K  Q  W  W  N  E  S  K  E  H  I  W  R   79
GCAATGATGTTCTCAATTAGGAGCAGATTAAAGGAGAAATTTGTGGATTTGTA
 A  M  M  F  S  I  R  S  R  L  K  E  K  F  V  W  I  C
AAAAGATGTTACGTTAAAGTAGAACCCCAGATATACAGGAGGATTCGAGAATGGGGAAGAGAT    360
 K  K  D  V  T  L  K  V  E  P  Q  I  Y  R  W  I  R  E  W  G  R  D  119
TATATGTCAAAATTACCCAAAGACAGGGGAAACTAAATGAAAATGTGCTAGTA
 Y  M  S  K  L  P  K  E  Q  G  K  L  N  E  K  C  A  S
AATTATACTATAATAATGGCAATATGTTATGTGCCTCTGTGCCATGATGCCTGTAAATCATAT    480
 K  L  Y  Y  N  M  A  I  C  M  L  P  L  C  H  D  A  C  K  S  Y   159
GATCAATGGATAACAAGGAAAAACAATGGATGTTTTGTCAACAAATTT
 D  Q  W  I  T  R  K  K  Q  W  D  V  L  S  T  K  F
CAAGTGTAAAGAAGACACAAAAAATCGGACGGAAAATATCGCAACAGCTTATGATATACTAAAA  600
 Q  S  V  K  K  T  Q  K  I  G  T  E  N  I  A  T  A  Y  D  I  L  K  199
CAGGAATTAAATGGATTTAAGAGGCGACTTTGAGAATGAAATTAACAAACGTG
 Q  E  L  N  G  F  K  E  A  T  F  E  N  E  I  N  K  R
```

FIG. 1B

```
ATAATTTATATAATCATTTATGCCCTTGTGTGCTGAGGAGGCTAGAAAGAATACCCAGGAAAT
 D  N  L  Y  N  H  L  C  P  C  V  V  E  E  A  R  K  N  T  Q  E  N   720
GTGAAAAATGTAGGAAGTGGTGTGTTGAATCTAAGGCAGCCAGAATCCGATAA            239
 V  K  N  V  G  S  G  V  E  S  K  A  A  A  N  P  I

CTGAAGCTGTAAAAAGTAGTAGCGGGGAGGGAGGTTCAGGAGGATTCTGCACACAAAAGTGTT
 T  E  A  V  K  S  S  S  G  E  G  K  V  Q  E  D  S  A  H  K  S  V   840
AACAAAGGTGAAGGTAAGTCTAGCACAAATGAAGCTGATCCCAGGTTCTCAATCAG         279
 N  K  G  E  G  K  S  S  T  N  E  A  D  P  G  S  Q  S
                         └──────── peptide 3 ──────────┘

GTGCTCCTGCTTCTCTGTAGTGTAGATGAGAAGGCAGGTGTTCCTGCTCTATCAGCTGGTCAAGGT
 G  A  P  A  S  R  S  V  D  E  K  A  G  V  P  A  L  S  A  G  Q  G   960
CATGATAAAGTTCCCCCTGCTGAAGCTGCTACAGAATCAGCTGTTCTGCATT             319
 H  D  K  V  P  P  A  E  A  A  A  T  E  S  A  V  L  H

CAGCAGACAAAACTCCAATACAGTAACAGAAGAAAATAAGGAAGAACCCAGATGGATGGTGCT
 S  A  D  K  T  P  N  T  V  T  E  E  N  K  E  G  T  Q  M  D  G  A   1080
GCGGGTGGGAGATGGTAAGGCCTCCGGTCCAACTGTTCTTCCGATGTTCCTAGTG          359
 A  G  D  G  K  A  P  G  P  T  V  S  S  D  V  P  S

TTGGGGGTAAGGATAGTGGTCCCAGTACCTCTGCGTCCCATGCTCTCGCTGGGGAAAATGGTGGA
 V  G  G  K  D  S  G  P  S  T  S  A  S  H  A  L  A  G  E  N  G  E   1200
GTTCATAATGGCACTGATACTGAACCTAAGGAAGATGGTGAGAAGGCTGATCCCC          399
 V  H  N  G  T  D  T  E  P  K  E  D  G  E  D  A  D  P
```

FIG. IC

```
AGAAAGATATAGAAGCAAGGGTAAGCAAGATCAAGATGATAGGTTCACAGGGTCACTTGGGCCA
 Q  K  D  I  E  V  K  G  K  Q  D  T  D  D  R  S  Q  G  S  L  G  P   1320
CATACTGATGAAAGAGCAACTTTGGGGGAAACTCATATGGAGAAGGATACAGAAA            439
 H  T  D  E  R  A  T  L  G  E  T  H  M  E  K  D  T  E

CCGCAGGAGGTAGTACTCTCACTCCCGAACAGAATGTTAGTGTTGCTTCTGATAATGGTAATGTT
 T  A  G  G  S  T  L  T  P  E  Q  N  V  S  V  A  S  D  N  G  N  V   1440
         DR.2 ends ─────┬──> DR.1 starts                             479
CCTGGATCTGGCAAT AACAAAATGAGGGTGCAACTGCGTTGAGTGGAGCTGAAA
 P  G  S  G  N  K  Q  N  E  G  A  T  A  L  S  G  A  E GTTTGAAATCAAACAGAAAGTGTACATAAAACTATTGATAATACAACTCACGGTTTAGAAAATAAA
 S  L  K  S  N  E  S  V  H  K  T  I  D  N  T  T  H  G  L  E  N  K   1560
AATGGAGGAAACGAAAAGGATTTCAAGAAGCACGATTTTATGAATAATGACATGT             519
 N  G  G  N  E  K  D  F  Q  K  H  D  F  M  N  N  D  M TGAATGATCAAGCAAGTTCTGATCACACAAGTTCAGACCAAACAAGTTCTGATCATACAAGTTCA
 L  N  D  Q  A  S  S  D  H  T  S  S  D  Q  T  S  S  D  H  T  S  S   1680
GATCAAACAAGTTCAGATCAAACAAGTTCTGATCACACAAGTTCTGATCAAACAA             559
 D  Q  T  S  S  D  H  T  S  S  D  H  T  S  S  D  Q  T GTTCAGATCAAACAAGTTCTGATCAAACAAGTTCGGAAGATATAGATACAGAAAGACACCAGGATAATGTCAGA
 S  S  D  Q  T  S  S  D  Q  T  I  D  T  E  G  H  H  R  D  N  V  R   1800
AATCCTGAAATAAAGAGTTCGGAAGATATGAGTAAAGGGGATTTTATGAGAAATT             599
 N  P  E  I  K  S  S  E  D  M  S  K  G  D  F  M  R  N
```

FIG. ID

```
CAAATAGTAACGAATTATATAGTCATATAATTGAATAATCGTAAATTAAATAGAGACCAATAC
 S  N  S  N  E  L  Y  S  H  N  N  L  N  N  P  K  L  N  R  D  Q  Y
GAACACAGAGATGTCAAAGCAACAAGGAGAAAATTATCCTTATGTCTGAAGTAA           1920
 E  H  R  D  V  K  A  T  R  E  K  I  I  L  M  S  E  V              639

ACAAATGCAATAATAGGGCATCCGTAAAATACTGTAACACTATAGAAGACAGAATGTTATCGAGC
 N  K  C  N  R  A  S  V  K  Y  C  N  T  I  E  D  R  M  L  S  S
ACTTGTTCAAGGGAGAGAGAAAATTTATGTTGTTCAATATCGGATTTTGTT              2040
 T  C  S  R  E  R  R  K  N  L  C  C  S  I  S  D  F  C              679
                 ↓
TGAATTATTTGAGCTCTATTCTTATGAATTTTATAATTGCATGAAAAAGGAATTTGAAGATCCA
 L  N  Y  F  E  L  Y  S  Y  E  F  Y  N  C  M  K  K  E  F  E  D  P
TCATACGAGTGCTTTACAAAGGAAGCTCCACAGGTATACAGGAAAAGATGATCA           2160
 S  Y  E  C  F  T  K  G  S  S  T  G                                712

ATAGACAAAGATGTTACGTACATTGAAAATAAATTCATTTTAGGAATGTTATAAATTTTTTGTA
ATCAATATTCTTTTTGCAGGCATAGTTATTTTGCCAGGGGGGAGCCTTTCTG             2280
          I  V  Y  F  A  T  G  G  A  F  L                         723

ATAATACTGCTACTATTGCCCTCATGAATGCAGCCTCGAATGAGTAACCAAAAAATATATAA
 I  I  L  L  F  A  S  W  N  A  A  S  N  D                         738
AATTAGAATAAGAATAAGAAATTAGAGTGGAAGCTAGATTAACAATTAAAATAAAA         2400

AATAAAAATAGAAAATGCTGTTAATGCACAATTAATTCTATATTCCATGTGTGCAATTTTAAGG
```

FIG. 1E

```
AGAGTAAAAATGTGAAATCATTATATGCATGCACGTATACATATAGACATATA              2520

TGTACCAATATATAATGCACACTTCCTTGTTCGTACAGTTATGAAGAAGCTACATTTGA        2640
        Y   E   E   E   A   T   F   D                              764

TGAGTTCGTGGAATATTCTGATGATATTCACAGAACCCCTCTAATGCCTAACGGT             2760
  E   F   V   E   Y   S   D   D   I   H   R   T   P   L   M   P   N  777

AATTCAAAATTCAAAAGCAAATTCATTTATGAAGAAATATTACACCATTCTGCATTATTCCTT

TTATTCTTCTTTAG ATATTGAGCACATGCAACATTTACACCCCTGATTATTC               2760
                |D   I   E   H   M   Q   F   T   P   L   D   Y   S |  777
                       C-terminal peptide
                  ← DR.1 ends ——

ATAATGCTACTTGGGTAAGTAAGGAGAATTGTGATAGTACAGCTGATGGAATTTTTGTCATTTTG  2880
CTTAATGCAGTAAATGAGAAGTATATGAACGGTTCGCAAAGAATGATTTAACAG              778

CACTATGACAATTACTTGTACTATGCGTCTTTATTTAAATATCTAAATTAGAATTTTTTG       3000
TATTTGTAATAAGTCAATACAAGTGTATTCCTTTTATTGGCTTGTAGGATGTGT

AGTCCTTTAGCCAATAGTAGAAAAATTCGTTTAGGCGAATTGTATAATTTCCTTTTTTTTTAT    3120
TTGAACTTTTTATTTTCTTATATTGACAAAAAAAAAAAATACC

ATTTCAATAATTTGAAAAAAAAAAAAAAAAAAAAAAAAAA                            3157
```

V1a V1c  V1a V1c

← origin
← 3.6 × 10⁶ bp
← 1.8 × 10⁶ bp
← 1.2 × 10⁶ bp

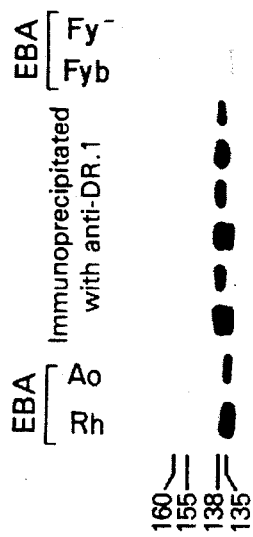
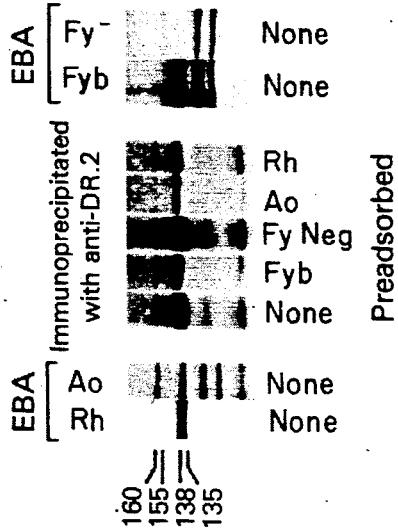
FIG. 6B
FIG. 6C
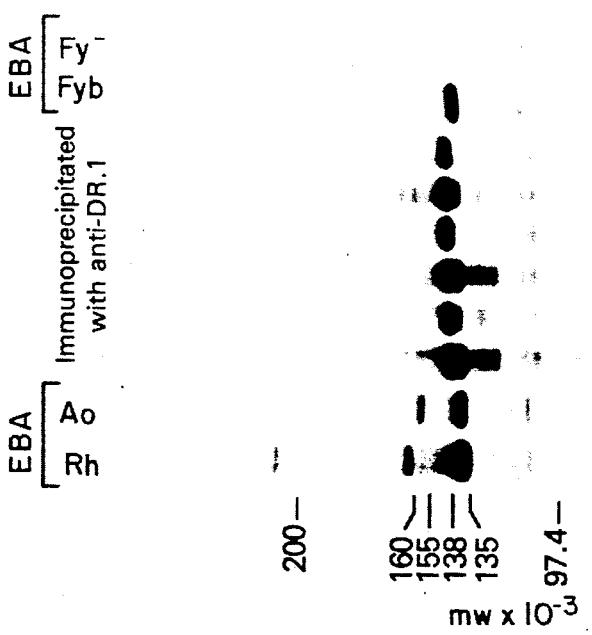
FIG. 6A

FIG. 8A 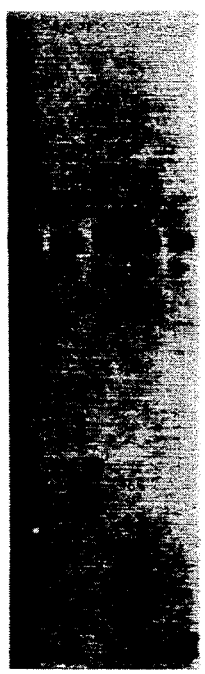 FIG. 8B  FIG. 8E EBA 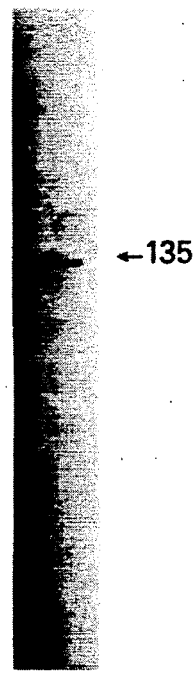
TX-100 pellet  supernatants
FIG. 8C  FIG. 8D  FIG. 8F EBA 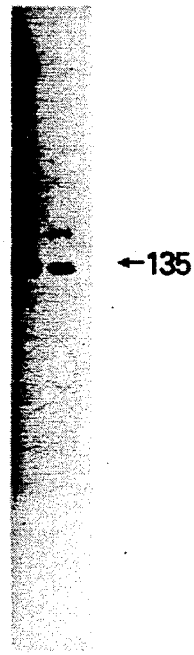
SDS pellet  supernatants FIG. 11A
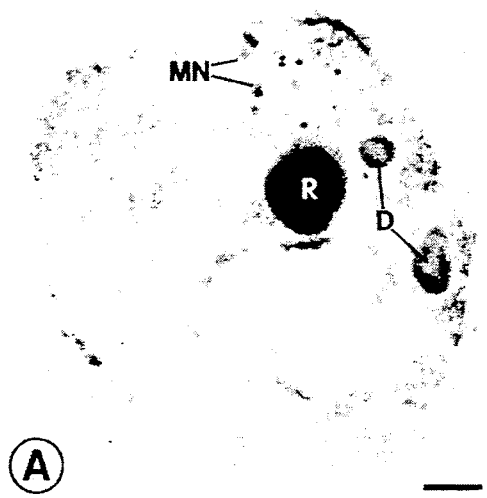
Ⓐ
FIG. 11B
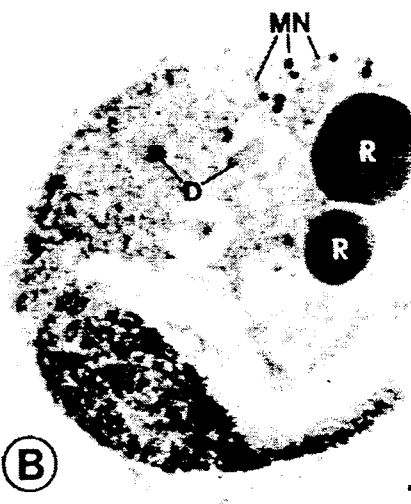
Ⓑ
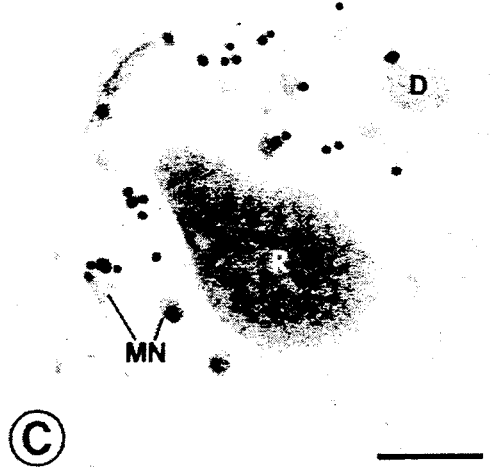
Ⓒ
FIG. 11C
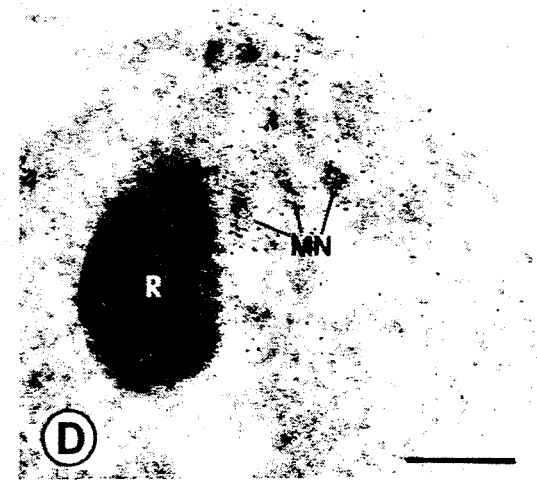
Ⓓ
FIG. 11D

FIG. 12A

```
                                                    AAGCTTTTAAAAATAGCAACAAAATTTCGAAACATTGCCA
CAAAAATTTTATGTTTTTACATATATTTAGATTCATAACAATTTAGG    85  V

TGTACCCGTGTTTTTTGATATATGCGCTTAAATTTTTTTTCGCTCATATGTTAGTTATATGTGTAGAACAACTT
GCTGAATAAATTACGTACACTTTCTGTTCTGAATATATTACCAC       205 V

ATACATTAATTTAATTTAAATACTATGAAAGGAAAAACCGCTCTTTATTGTTCTCCCTAGTTTTATTATTGTTACAC
AAGGTATCATATAAGGATGATTTTCTATCACACTAATAAATTAT      325 V
             M K G K N R S F V L L L L L L H
             K V S X K D D F S I T L I N Y    33  V
                     signal peptide CATGAAGGAAAAATATATTAATTATACTAAAAGAAAATTAGAAGCTAATAATCGTGATGTTTGCAATTTT
TTTCTTCATTTCTCTCAGTTAAATAATGTATTATTAGAACGAACA      445 V
 H E G K K Y L I L K R K L E K A N N R D V C N F
 F L H F S Q V N N V L L E R T                    73  V ATTGAAACCCTTCTAGAATGCAAAATGAATATGTGAAAGGTTATAAATTAGCTAAAGGACACCAC
TGTGTTGAGGAAGATAACTTAGAACGATGGTTACAAGGAACCAAT     565 V
 I E T L L E C K N E Y V K G E N G Y K L A K G H H
 C V E E D N L E R W L Q G T N                    113 V GAAAGAAGAAGTGAGGAAAATATAAAATATGAGTAACGAACTAAAAATAAAGTATGCGCAAATGAAT
GGAAAAGAAGCAGCCCGCATTTTGAAGGAATCAATTTACGGGGCG     685 V
 E R S E E N I K Y K Y G V T E L K I K Y A Q M N
 G K R S S R I L K E S I Y G A                    153 V
```

FIG. 12B

```
CATAACTTTGGAGGCAACAGTACATGGAGGAGAAAGATGGAGGAGAAACTGGGAGGAGAAAAGATGGAGAA
CATAAAACTGATAGTAAACTGATAACGGGAAAGTGCAAACAAT                                805 V
 H  N  F  G  G  N  S  Y  M  E  G  K  D  G  G  D  K  T  G  E  E  K  D  G  E
 H  K  T  D  S  K  T  D  N  G  K  G  A  N  N                                193 V

TTGGTAATGTTAGATTATGAGACATCTAGCAATGGCCAGCCAGCGGGAACCCTTGATAATGTTCTTGAATTGTG
ACTGGGCATGAGGGAAATTCCTAAAAATTCCTCGAATGGTGGC                                925 V
 L  V  M  L  D  Y  E  T  S  S  N  G  Q  P  A  G  T  L  D  N  V  L  E  F  V
 T  G  H  E  G  N  S  R  K  N  S  S  N  G  G                                233 V

AATCCTTACGATATTGATCATAAGAAAACGATCTCTAGTGCTATTATAATCATGCTTTTCTTCAAAATACTGTA
ATGAAAAACTGTAATTATAAGAGAAAAACGTCGGGAAAGAGATGG                              1045 V
 N  P  Y  D  I  D  H  K  K  T  I  S  S  A  I  I  N  H  A  F  L  Q  N  T  V
 M  K  N  C  N  Y  K  R  K  R  E  R  D  W                                   273 V

GACTGTAACACTAAGAAGGATGTTTGTATACCAGATCGAAGATATCAATTATGTATGAAGGAACTACGAATTTG
GTAAATAATACAGACACAAATTTCATAGGGATATAACATTTCGA                               1165 V
 D  C  N  T  K  K  D  V  C  I  P  D  R  R  Y  Q  L  C  M  K  E  L  T  N  L
 V  N  N  T  D  T  N  F  H  R  D  I  T  F  R                                313 V

AATTATATTTGAAAAGGAAACTTATTTTATGATGCTGCAGTAGAGGGCGATTTATTACTTAAGTTGAATAACTAC
AGATATAACAAGACTTTGCAAGGATATAAGATGGAGTTTGGGA                                1285
 K  L  Y  L  K  R  K  L  I  Y  D  A  V  E  G  D  L  L  L  K  L  N  N  Y
 R  Y  N  K  D  F  C  K  D  I  R  W  S  L  G  *  *  *  *  *  *  *  *  *    353
```

FIG. 12C

```
GATTTGGAGATATAATTATGGAACGGATATGGAAGGCATCGGATATATTCCAAAGTAGTGAAAATAATTGCGC
AGCATCTTTGGAACTTTGATGAGAAAGGCCCAACAGCGTCGTAAACAG             1405 V
D  F  G  D  I  M  G  T  D  N  E  G  I  G  Y  S  K  V  V  E  N  N  L  R
S  I  F  G  T  D  E  K  A  Q  Q  R  R  K  Q  *  393 V *  *  *  *  *  *
*  *  *  *  *  *  *  *  *  N  *  *  *  *  *  Q  *  *  *  *  *  *  *
Q  *  V  *  *  *  *  *  *  K  *  *  D  *  *  *        K

TGGTGGAATGAATCTAAAGCACACAAATTTGGACAGCAATGATGTACTCAGTTAAAAAAGATTAAGGGAATTTT
ATATGGATTTGTAAATTAAATGTTGCGGTAAATATAGAACCGCAG             1525 V
W  W  N  E  S  K  A  Q  I  W  T  A  M  M  Y  S  V  K  K  R  L  K  G  N  F
I  W  I  *  *  K  L  N  V  A  V  N  I  E  P  Q  *  433 V *  *  *  *  *  *

ATATAGAGATGGATTCGAGAATGGGAAGGATTACGTGTCAGAATTGCCCACAGAAGTGCAAAACTGAAAGAA
AAATGTGATGGAAAATCAATTATACTGATAAAAGTATGTAAG             1645 V
I  Y  R  W  I  R  E  W  G  R  D  Y  V  S  E  L  T  E  V  Q  K  L  K  E
K  *  D  G  K  I  N  Y  T  D  K  K  V  *  K  *  473 V *  *  Q  G  *  N  *
*  *  *  *  *  *  *  *  *  *  *  *  M  *  *  K  *  *  *  *  *  *  *  *
*  *  *  A  S  *  L  Y  *  N  M  A  I  *  M      K

GTACCACCATGTCAAAATGCGTGTAAATCATATGATCATATGATAACCAGAAAAAAATCAATGGATGTCTG
TCAAATAATTCATAAGTGTAAAACGCAGAAAAGGTTCAGACG             1765 V
V  P  P  Q  N  A  K  S  Y  D  Q  W  I  T  R  K  K  N  Q  W  D  V  L
S  N  K  F  I  S  V  K  N  A  E  K  V  Q  T  *  513 V *  *  K  *  *  *  *
L  *  L  *  H  D  *  *  *  *  *  *  *  I  G  *  *  *  *  *  *  *  *  *
*  T  *  *  S  *  *  *  K  T  Q  *            K
```

FIG. 12D

```
GCAGGTATCGTAACTCCTTATGATATACTAAAACAGGAGTTAGATGAATTAACGAGGTGGCTTTTGAGAATGAA
ATTAACAAACGTGATGGTGCATATATTGAGTTATGCGTTTGTTCC         1885 V
 A  G  I  V  T  P  Y  D  I  L  K  Q  E  L  D  E  F  N  E  V  A  F  E  N  E
 I  N  K  R  D  G  A  Y  I  E  *  L  *  V  C  *  *  N  G  *  K  *  A  T  *
 E  N  *  A  *  *  N  L  *  *  N  H  *  *  *  *  *  R  *  *  V  *  K  *  *
 *  *  *  *  *  *  *  *  *  *  *  *  *  *  *  *  *  *  *  *  *  *  K  *  *
                                                       553 V

GTTGAAGAGGCTAAAAAGAATACTCAGGAAGTGTGACAATGTGGACAATGCTGCTAAATCTCAGGCCACCAAT
TCAAATCCGATAGTCAGCCTGTAGAGTAGTAAAGCGGAGAAG           2005 V
 V  E  E  A  K  K  N  T  Q  E  V  T  N  V  D  N  A  A  K  S  Q  A  T  N
 S  N  *  I  S  Q  *  N  V  D  S  S  K  A  E  K  *  G  S  G  V  E  *  K  S
 *  *  *  *  R  *  *  T  E  A  *  K  *  *  N  *  *  *  *  G  *  *  K  *  A
 *  *                                                    G     K
                                                       593 V

GTTCCAGGAGATTCTACGCCATGGAAATGTTAACAGTGGCCAAGATAGTTCTACCACAGGTAAAGCTGTACGGGG
GATGGTCAAAATGGAAATCAGAGACACCTGCAGAAAGCGATGTACAG       2125 V
 V  P  G  D  S  T  H  G  N  V  N  S  G  Q  D  S  T  T  G  K  A  V  T  G
 D  G  Q  E  N  G  N  Q  T  A  E  S  D  V  Q  *  E  G  K  *  S  *  N  E  *
 *  Q  *  A  *  K  S  *  *  K  S  *  K  E  G  K  *  S  *  *  N  E  *  D  *
 Q  S  G  A  P  A  S  R  S  V  D  E  K  A                 K
                                                       633 V
```

FIG. 12E

```
CGAAGTGATATTGCCGAAAGTGTAAGTGTACTAAAATGTTGATCCGCAGAAATCTGTAAGTAAAAGAAGTGACGAC
ACTGCAAGCCGTTACAGTTATTGCCGAAGCTGGAAGGACAAAACTTA    2245 V
 R  S  D  I  A  E  S  V  S  A  K  N  V  D  P  Q  K  S  V  S  K  R  S  D  D
 T  A  S  V  T  G  I  A  E  A  G  K  E  N  L         673 V
 G  V  A  L  S  A  G  Q  G  H  D  K  V  *  P  A  E  A  A  T  E  S  A
 V  L  H  S  A  D  K  T  P  N  T  V  T  E  E     K

GGGCGCATCAAATAGTCGACCTTCTGAGTCCACCGTTGAAGCAAATAGCCCCAGGTGATGATACTGTGAACAGTGCA
TCTATACCTGTAGTGAGTGGTGAAACCCATTGGTAACCCCCTAT    2365 V
 G  A  S  N  S  R  S  E  S  T  V  E  A  N  S  P  G  D  D  T  V  N  S  A
 S  I  N  V  S  G  E  N  L  V  T  Y         713 V
 N  K  E  G  T  Q  M  D  G  A  A  G  D  K  A  P  G  M  T  V  S  *  D
 V  *  S  *  V  G  G  K  D  S  G  *     K

AATGGTTTGAGGCATTCGAAAGACAATAGTGATAGCGATGGACCTGCGAATCAATGGCGAATCCTGATTCAAAT
AGTAAAGGTGAGACGGGAAAGGGCAAGATGATATGGCGAAG    2485 V
 N  G  L  R  H  S  K  D  N  S  D  S  D  G  P  A  E  S  M  A  N  D  S  N
 S  K  G  E  T  G  K  G  Q  D  N  D  M  A  K         753 V
 T  S  A  S  *  A  L  A  G  E  N  G  E  V  H  N  G  T  D  T  E  *  K  E  D
 G  E  K  A  D  P  Q  K  D  I  E  V  K  G  *     K

GCTACTAAAGATAGTAGTAATAGTTCAGATGTTACCAGCTCTGCTACGGGTGATACTACTGATGCAGTTGATAGG
GAAATTAATAAAGGTGTTCCTGAGGATAGGGATAAAAACTGTAGGA    2605 V
 A  T  K  D  S  N  S  S  D  G  T  S  S  A  T  G  D  T  T  D  A  V  D  R
 E  I  N  K  G  V  P  E  D  R  D  K  T  V  G         793 V
 Q  D  T  *  D  R  S  Q  G  L  G  P  H  T  D  E  R  A  *  L  G  E  T  H
 M  E  K  D  T  E  T  A  G  G  S  T  L  P     K
```

```
GTTATAAACATTTTTGTACCCAAAATTCTTTTTGCAGACAAGACTTACTTTGCCGCGGGAGCGTTGCTGATA
CTGCTGTGTTGTTAATTGCTTCAAGGAAGATGATCAAAAATGAGTAA                3565 V
           intron I ends→1D K T Y F A C K T T I
                        R K M I K N D1→         1077 V
                                      G I V * * * T C *
                        * * * W N A A S *
                                        *         K
                                      transmembrane region
                       cytoplasmic tail
CCAGAAAATAAAATAAAATAACATAAAATAAAACTAGAATAACAATTAAAATAAATAAAATGAGAAAT
GCCTGTAATGCACAGTTAATTCTAACGATTCCATTGTGAAGTT                   3685 V
intron II starts
TTAAAGAGAGCACAAATGCATAGTCATTATGTCCATGCATATATACACATATGTACGTATATATAATAACGC
ACACTTTCTGTCGTACAGTTCTGAAGAAGCTACATTTAATGAG                   3805 V intron II ends→1 S E E A T F N E          1085 V
              Y E * * * * D *            K TTTGAAGAATACTGTGATAATATTCACAGAATCCCTCTGATGCCTAACAGTAATTCAAGAGCAAATT
CCATTAAAAGAAAATGTTACATCATTTGCGTTTTCTTTTT                      3925 V
                                    1→intron III starts
                                          1102 V
F E E Y C D N I H R I P L N P N *
* V * S * D * * * T * * * *              K
```

FIG. 12I

```
CTTTTTTTTCTTTTTTAGATATTGAACACATGCAGCCATCAACCCCCCTGAATTATTCATGATGCTACTTTGG
TAAGTAAAGCAATTCTGATTGTAGTGCTGATGTAATTTAGTCA        4045 V
intron III ends→→IN  I  E  H  M  Q  P  S  T  R  L  D  Y  S
                                              1115 V
                D  *  *  *  *  Q  F  *  *  *  *  *  *  *
                                                 K

TTTTGCTTGCTGCAATAAACGAGAAAATATATCAAGCTT
```

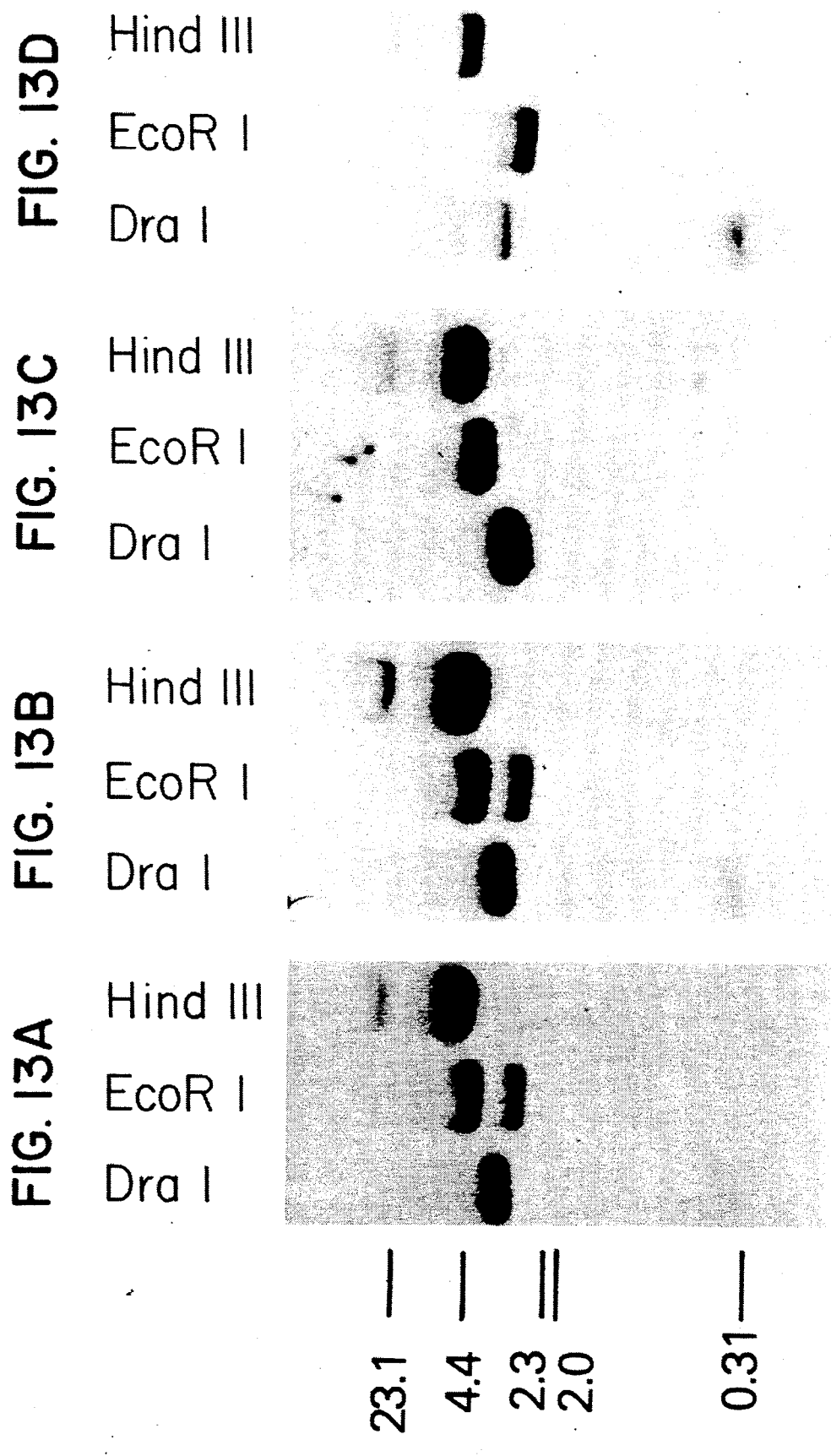

FIG. 14

INTRON I

```
exon I   intron I
v ...AAG/GTATGCAGAGAAAAGATGCTGAATAGAGAAAGGTGTTGAGTAAATTAAAAAGGAATTAATTTTAGGAATGTTATAAACATTTTGTACCCAAAATCTT
        ::: ::: ::::::: :::::::::                           ::::: ::: ::::::: ::: :::
k ...CAG/GTATACAGGAAAGATGATCAATAGACAAAGATGTTACGTACTACGTACATTGAAATAAATTCATTTTAGGAATGTTATAAATTTTTTGTAATCAATATTCTT
```

INTRON II

```
       exon II
v  TTTG-CAG/ACA...
   :::  ::: :::
k  TTTTGCAG/GCA...
```

```
exon II   intron II
v ...TGA/GTAACCAGAAAATAAATAAAT----------AACATAAATAAAATAAAACTAGAATAACAATTAAATAAAATAA-AATGAGAAATGCCTGTTA
       ::: :::::::::::: :::::              :::  ::: :::::  :::: ::::: :::::::::::::   ::::::::::::::::
k ...TGA/GTAACCAAAAATAATATAAAATAATATAAAATTAGAATAAGAATAAGAGTGGAAGCTAGATTAACAATTAAACAATTAAATAAAATAAATAGAAAATGCTGTTA
```

```
v ATGCACAGTTAATTCTAACGATTCCATTTGTGAAGTTTTAAAGAGAGCACAAATGCATAGTCATTATGTCCATGCA----------TATATACACATATATGTACGT
   :::::::: ::::  ::::  ::: :::::::::::: :::::::: ::::::::  ::::::: :::::::::::          :::::::::: :::::::::
k ATGCACAATTAATTCTATATATTCCATGTGTGTGCAATTTGTTGCAAATCATTATGTGAAATCATTATGCATGCACGTATACATATGAGACATATATGTACCA
```

INTRON III

```
v ATATATAATAAACGCACACTTTCTGTTCGTACAG/TTC...
   ::::::::: :  :::::::::: :::::::::  :::
k ATATAATAAT-GCACACTTCCTGTTCGTACAG/TTA...
```

```
exon III   intron III                                                                                    exon IV
v ...ACA/GTAATTCAAATTCAAGAGCAAATTCCATTTAAAAAGAAATGTTACATCATTTGCGTTTTCTTTTTTTCTTTTTTTAG/ATA...
       ::: :::::::::::::::::::: ::::::: :::::: :::::::::  ::: :::: :::  :::          :::  :::
k ...ACG/GTAATTCAAATTCAAAAGCAAATTCATTTATGAAGAAATATTACACCATTCTGCATTATTCCTTTTA----------TTTCTTCTTTTAG/ATA...
```

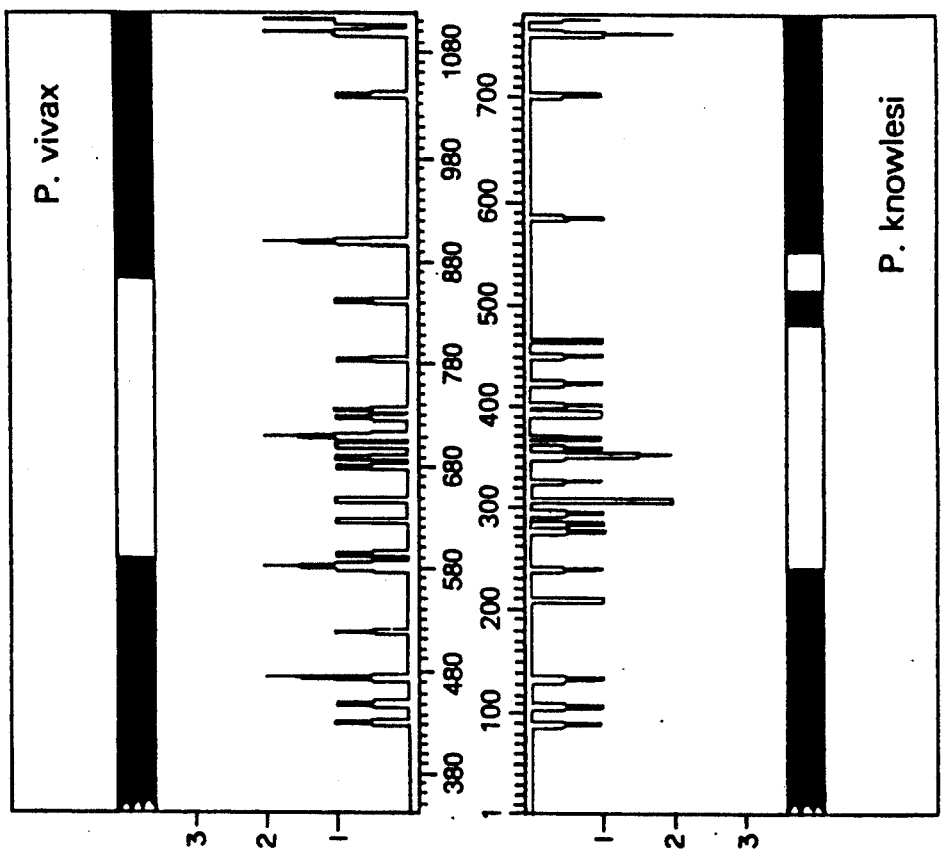
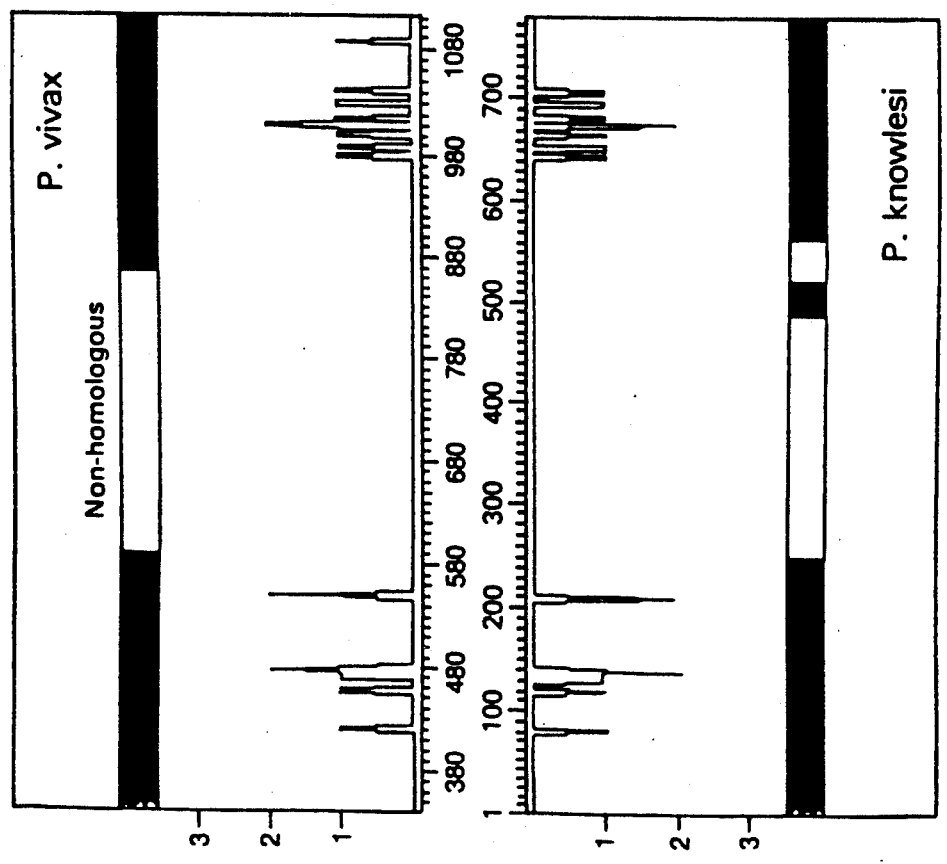
FIG. 16B1  FIG. 16B2
FIG. 16A1  FIG. 16A2

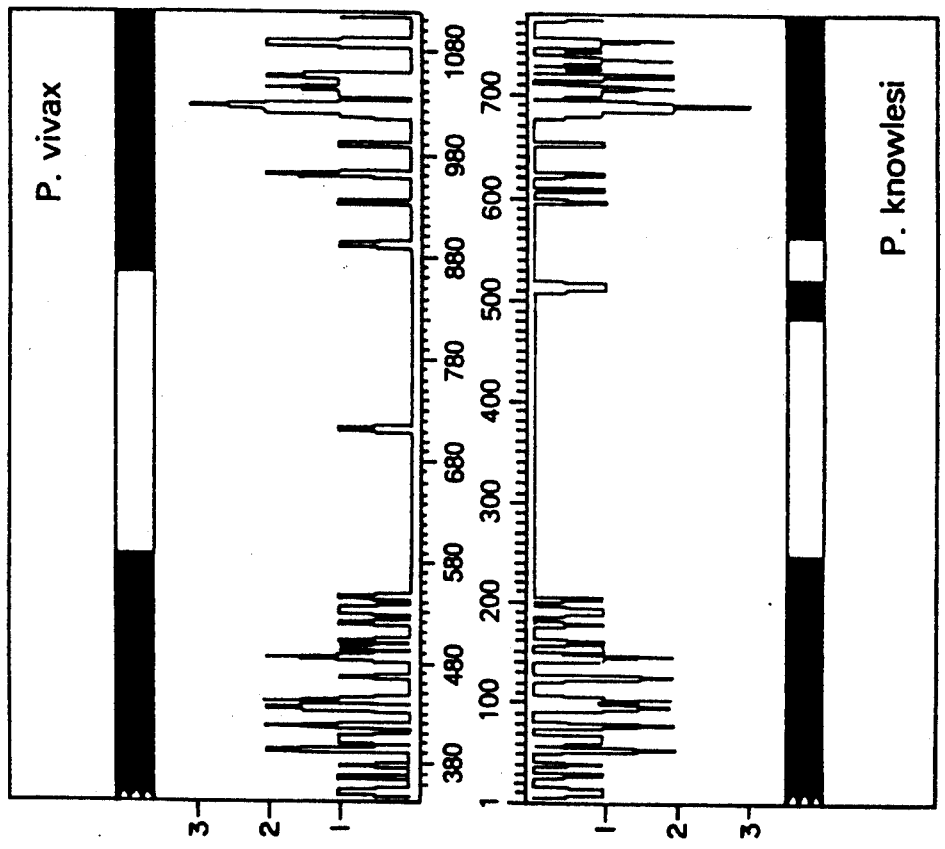

DNA ENCODING *PLASMODIUM VIVAX* AND *PLASMODIUM KNOWLESI* DUFFY RECEPTOR

BACKGROUND OF THE INVENTION

1. Field of the Invention

The present invention relates to the Duffy receptor of a Plasmodium, particularly Plasmodium knowlesi and Plasmodium vivax Duffy receptors.

2. Background Information

Duffy positive blood group determinants on human erythrocytes are essential for invasion of human erythrocytes by *Plasmodium vivax*, a human malaria, and by *P. knowlesi*, a malaria of old world monkeys that invades human erythrocytes [Miller et al., Science 189: 561–563 (1975) and Miller et al., N. Engl. J. Med. 295: 302–304 (1976)]. During invasion, a merozoite first attaches to an erythrocyte on any surface of the merozoite, then reorients such that its apical end is in contact with the erythrocyte [Dvorak et al., Science 187: 748–750 (1975)]. Both attachment and reorientation of *P. knowlesi* merozoites occur equally well on Duffy positive and negative erythrocytes [Miller et al., Science 189: 561–563 (1975)]. A junction then forms between the apical end of the merozoite and the Duffy-positive erythrocyte, followed by vacuole formation and entry of the merozoite into the vacuole [Aikawa et al., J. Cell Biol. 77: 72–82 (1978)]. Junction formation and merozoite entry into the erythrocyte do not occur on Duffy negative cells [Miller et al., J. Exp. Med. 149: 172–184 (1979)], suggesting that a receptor specific for the Duffy determinant is involved in apical junction formation but not initial attachment.

The apical end of merozoites is defined by the presence of three organelles: rhoptries, dense granules, and micronemes. The contents of the rhoptries discharge onto the erythrocyte membrane after apical junction formation, presumably to form the vacuole into which the parasite enters [Ladda et al., (1969); Bannister et al., (1975) and Aikawa et al., (1978)]. The dense granules release substances into the vacuolar space after the apical end has entered the vacuole [Bannister et al., (1975) and Torii et al., Infection and Immunity 57: 3230–3233 (1989)]. The function of the micronemes has been unknown. Nevertheless, the location of these organelles suggest they are involved in the mechanism of invasion.

Duffy binding proteins are defined biologically as those soluble proteins that appear in the culture supernatant after the infected erythrocytes release merozoites, the invasive stage, and that bind to human Duffy positive and not to human Duffy negative erythrocytes. A 135 kDa protein in *P. vivax* and *P. knowlesi* has been studied in greatest detail. Its binding to Duffy positive erythrocytes is blocked by antisera to the Duffy blood group determinants and purified Duffy blood group antigens and it binds specifically in the region of the Duffy blood group determinant on Western blots.

A soluble 135 kDa protein from *P. knowlesi* culture supernatant was identified that specifically binds the Duffy blood group determinants [Haynes et al., J. Exp. Med. 167: 1873–1881 (1988) and Miller et al., Mol. Biochem. parasitol. 31: 217–222 (I988)]. An analogous protein of 135 kDa has been found in the Culture supernatant of *P. vivax* which binds specifically to the Duffy blood group determinants [Wertheimer et al., Exp. Parasitol. 69, 340–350 (1989) and Barnwell et al., J. Exp. Med. 169: 1795–1802 (1989)]. The specificity of binding and immunochemical data indicate that the soluble 135 kDa protein or a membrane bound form of this protein is the Duffy receptor. There are four major Duffy phenotypes of human erythrocytes, Fy(a), Fy(b), Fy(ab), and Fy(negative), as defined by the anti-$Fy^a$ and anti-$Fy^b$ sera [Hadley et al., In Red Cell Antigens and Antibodies, G. Garratty, ed. (Arlington, Va.: American Association of Blood Banks) pp. 17–33 (1986)]. More *P. knowlesi* Duffy binding protein binds to human Duffy b erythrocytes than to Duffy a erythrocytes; none bind to Duffy negative erythrocytes [Haynes et al., J. Exp. Med. 167: 1873–1881 (1988)]. The *P. vivax* Duffy binding proteins bind equally to Fya and Fyb erythrocytes. The *P. knowlesi* Duffy binding proteins also bind to rhesus erythrocytes, but the *P. vivax* Duffy binding proteins do not bind to rhesus erythrocytes. This binding correlates with the susceptibility of these erythrocytes to invasion by *P. knowlesi* and *P. vivax*. The binding specificities probably reflect the differences in the Duffy blood group antigens of the host to which the parasite has adapted.

SUMMARY OF THE INVENTION

It is an object of the present invention to provide the gene encoding the Duffy receptor of a Plasmodium parasite.

It is another object of the present invention to characterize and localize the Duffy receptor with and secreted from the Plasmodium parasite.

It is a further object of the present invention to provide a vaccine for humans against malaria and related organisms.

It is yet a further object of the present invention to provide a means of identifying molecules analogous to the Duffy receptor in *P. falciparum*, *P. ovale* and *P. malariae* for use in a malaria vaccine.

Various other objects and advantages of the present invention will become obvious from the drawings and the following description of the invention.

In one embodiment, the present invention relates a DNA segment encoding all, or a unique portion of a Duffy receptor of a Plasmodium parasite.

In another embodiment, the present invention relates to a Plasmodium Duffy receptor protein separated from proteins with which it is naturally associated.

In further embodiment, the present invention relates to a recombinant DNA molecule comprising a DNA segment encoding all, or a unique portion, of a Duffy receptor of a Plasmodium parasite and a vector. The invention also relates to a host cell comprising the recombinant DNA molecule which expresses the Duffy receptor protein and to a method of producing a recombinant Duffy receptor.

In another embodiment, the present invention relates to a purified form of an antibody specific for a Duffy receptor.

In a further embodiment, the present invention relates to a vaccine against malaria comprising all, or a unique portion, of a Duffy receptor protein, in an amount sufficient to induce immunization against malaria, and a pharmaceutically acceptable carrier.

In yet a further embodiment, the present invention relates to a method of disrupting the Plasmodium life cycle in humans by administering antibodies specific for the binding site of the Duffy receptor in an amount sufficient to inhibit the receptor from binding red blood cells in the human.

BRIEF DESCRIPTION OF THE DRAWINGS

FIGS. 1A to E. Nucleotide sequence and deduced amino acid sequence of the genomic DNA clone pEco6 from *P. knowlesi*.

Figure 2A:
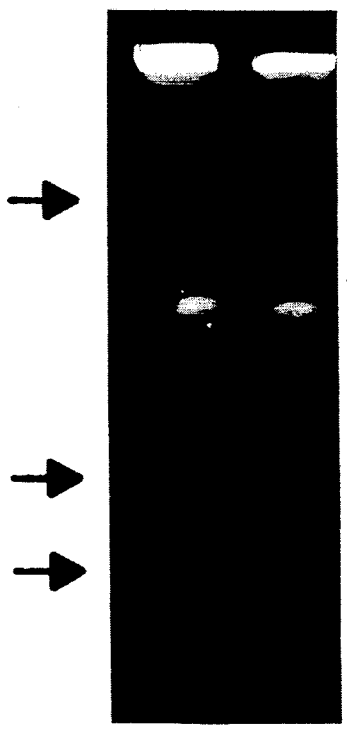

Cysteine residues are highlighted by reverse print and proline residues are highlighted in a shaded box. The pentapeptide repeats SSD(H/Q)T are underlined and a predicted transmembrane spanning hydrophobic sequence is shaded. The exon/intron splice junctions are indicated with small arrows over the sequence (GTA... .YAG). Enclosed in the boxes with a dashed line are putative polyadenylation sites; the polyadenylate tail, in italics, is in the sequence position found in the cDNA clone 1C1. The start and end of regions DR.1 and DR.2 are indicated over the sequence. Region DR.1 begins at bp 1403 (amino acid 467) and ends at bp 2437 (amino acid 778). Region DR.2 begins at bp 117 (amino acid 39) and ends at bp 1400 (amino acid 465). Oligonucleotides (30 and 13) and peptides (3 and the C-terminal) are enclosed in boxes.

FIGS. 2A and B. Genes of the Duffy receptor family are on three chromosomes in *P. knowlesi*. (A) Chromosomes prepared from two *P. knowlesi* clones V1a and V1c were separated by pulsed-field gel electrophoresis and stained with ethidium bromide. (B) Insert of p2C1 was radiolabeled by the random priming method and hybridized chromosomes of 3 sizes ($1.2 \times 10^6$, $1.8 \times 10^6$, $3.6 \times 10^6$ bp). Chromosome sizes were determined previously relative to their migration to *P. falciparum* chromosomes (Hudson et al., 1988).

Figure 3A:
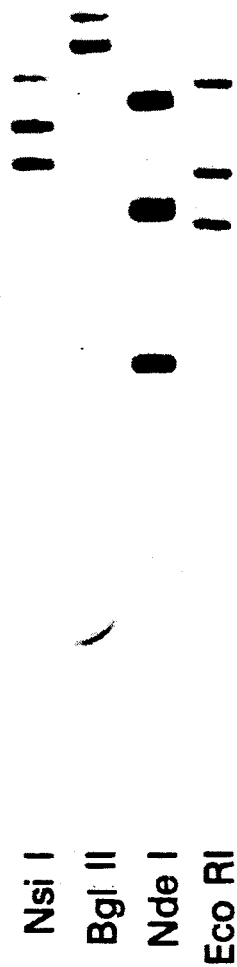
Figure 3B:
Figure 3C:
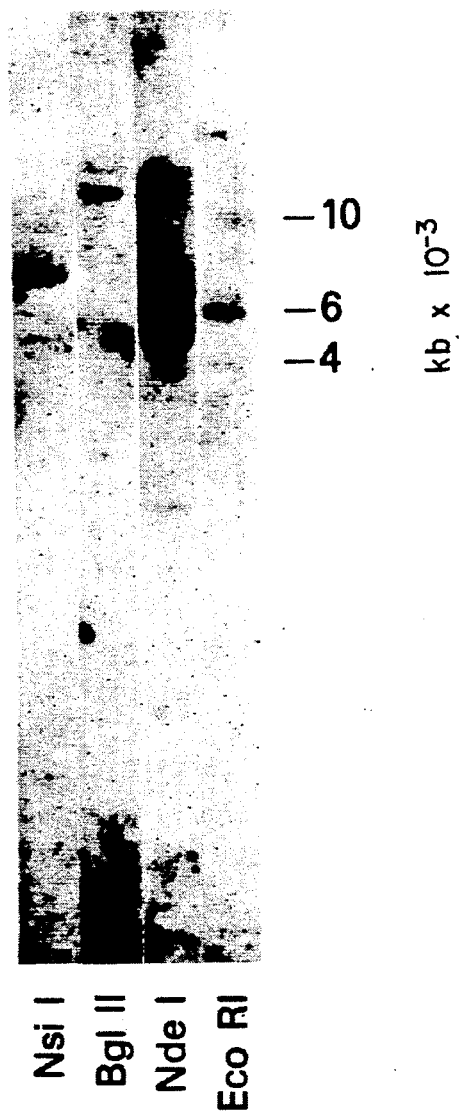

FIGS. 3A to C. Identification of restriction fragments from the Duffy receptor gene in *P. knowlesi*.

(A) Southern blot of the *P. knowlesi* genomic digest probed with DR.1.

(B) Southern blot of the *P. knowlesi* genomic digest probed with DR.2.

(C) Southern blot of the *P. knowlesi* genomic digest probed with oligonucleotide 13. Molecular weights were calculated from known restriction digest fragments of cDNA (Hind III) and φX 174 RFDNA (Hae III).

Figure 4:

FIG. 4. Structure of the 6 kb EcoRI genomic fragment and sequence relatedness to other members of the *P. knowlesi* gene family. The exons of the predicted open reading frame of the 6 kb EcoRI fragment are shown as boxes and the introns as lines. The 5' end is shown as a jagged line to indicate incomplete sequence in this region. Oligonucleotide probes derived from the 6 kb EcoRI *P. knowlesi* gene fragment were used to probe genomic digests of *P. knowlesi* and *P. vivax* southern blots. Genomic DNA was digested with multiple restriction enzymes (*P. knowlesi*: EcoRI, EcoRI/BamHI, EcoRI/DraI, NsiI, NsiI/BamHI, NsiI/DraI; *P. vivax*: EcoRI, HindIII, DraI, KpnI), separated by agarose gel electrophoresis, denatured and blotted on to GeneScreen Plus (DuPont). Oligonucleotides were radiolabeled and hybridized as described in FIG. 3. Melting point ($T_m$) was estimated using the formula $T_m = (\% \text{ GC})(0.41) + 81.5 - (675/\text{ number of bases in oligonucleotide probe})$. Blots were stripped with 0.5M NaOH, 1.5M NaCl between hybridizations.

Figure 5:
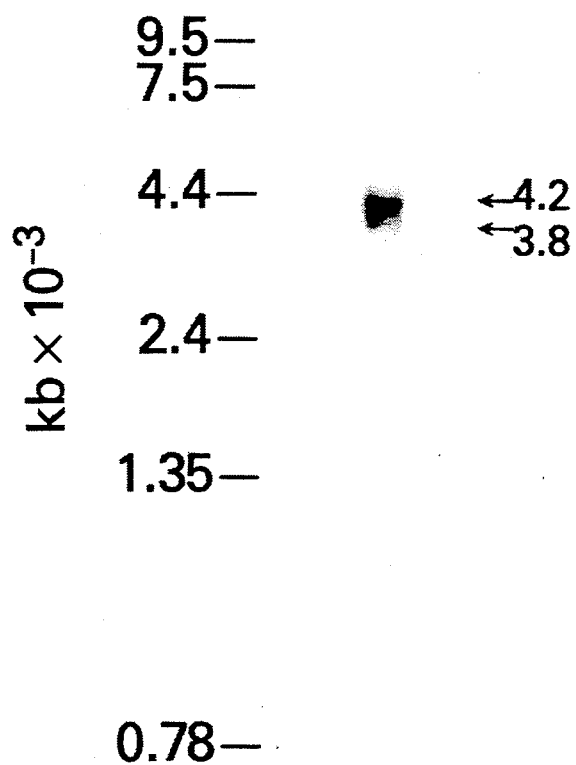

FIG. 5. Identification of RNA transcripts of the Duffy receptor gene family. PolyA enriched RNA from late-stage schizonts of *P. knowlesi* was separated by agarose gel electrophoresis (1% agarose, 20 mM MOPS, 5 mM sodium acetate, 0.5 mM EDTA, 200 mM formalin), transferred onto GeneScreen Plus in 20X SSC, crosslinked onto the membrane with ultraviolet, and dried under vacuum. Insert of p1C1 was radiolabeled by the random priming method and hybridized to two closely migrating transcripts of 3.8 and 4.2 kb in 6×SSC, 20 mM HPO., pH 6.8, 5× Denhardts', 0.5% SDS, 100 μg/ml sodium Heparin and 50 μg/ml sheared salmon sperm DNA at 65° C. overnight, and had a final wash in 0.1X SSC, 0.1% SDS at 55° C.

FIGS. 6A to C. Immunochemical analysis of Duffy receptor family proteins from *P. knowlesi* culture supernatants.

Culture supernatants were immunoprecipitated with (A,B) anti-DR.1 or (C) anti-DR.2 rabbit serum. Culture supernatants were first adsorbed or not adsorbed with human or primate erythrocytes as indicated. Abbreviations used: Duffy positive human (Fyb); monkey RBC (Ao, Aotus; Ce, Cebus; Rh, rhesus); Duffy negative human RBC (Fy Neg); and erythrocyte binding assay (EBA).

Figure 7:
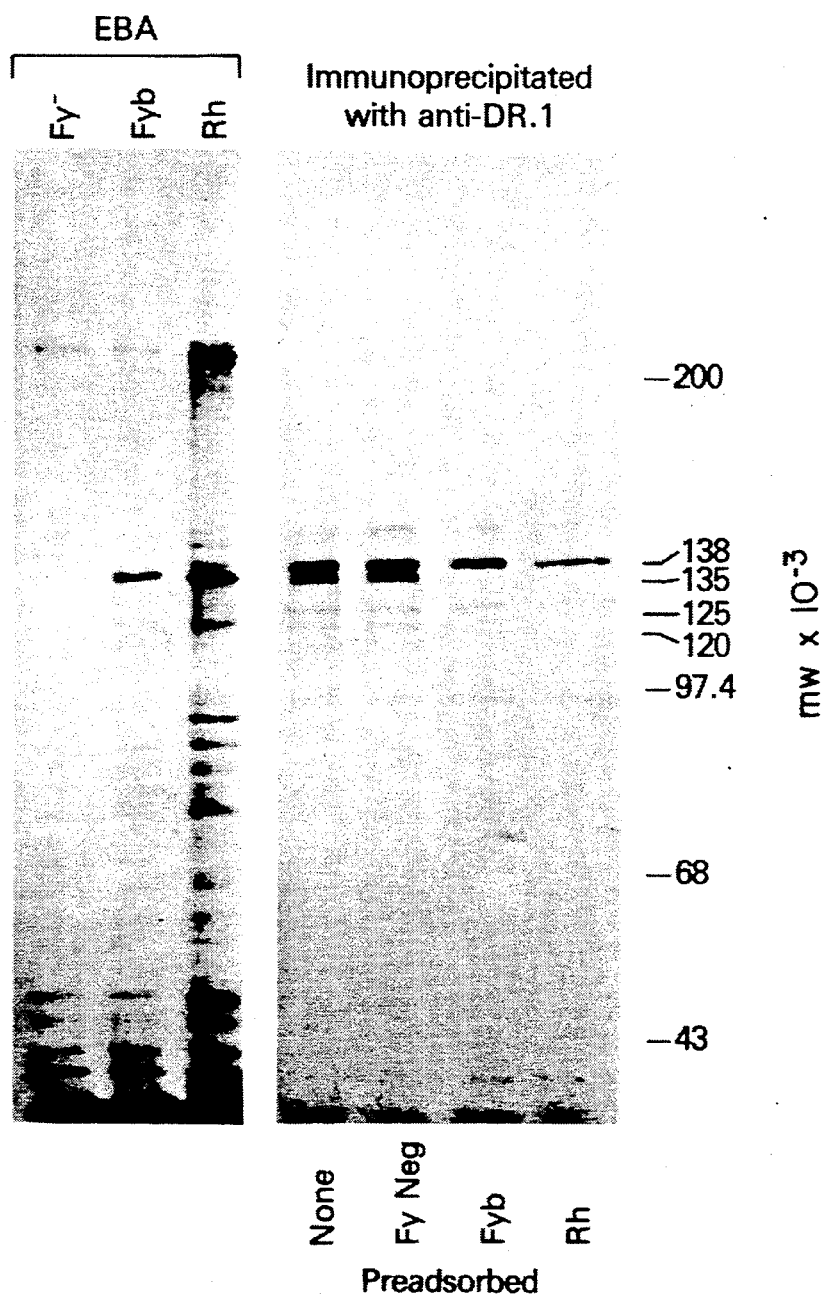

FIG. 7. Analysis of *P. knowlesi* soluble rhesus-specific erythrocyte binding proteins of the Duffy receptor family. Metabolically-labeled *P. knowlesi* culture supernatant was untreated or preadsorbed with two volumes of packed cell volumes of washed erythrocytes of Human Duffy negative (Fy Neg), Human Duffy b positive (Fy b), and Rhesus erythrocytes (Rh), instead of one volume of packed cells as in FIG. 6, and immunoprecipitated with anti-DR.1 rabbit sera. Erythrocyte binding proteins of rhesus, human Duffy b, and human Duffy negative erythrocytes were affinity-purified in erythrocyte binding assays (EBA) from the same culture supernatants as the immunoprecipitated proteins and were electrophoresed on the same SDS-PAGE gel. The relative molecular weights of the immunoprecipitated proteins were calculated from prestained molecular weight standards of 200, 97.4, 68, and 43 kDa (Bethesda Research Laboratories) and adjusted relative to the 135 kDa protein. The SDS-PAGE gel contained 0.8% bis crosslinker, mixed-length SDS and was 0.75 mm thick.

FIGS. 8A to F. Pulse-chase analysis of *P. knowlesi* Duffy receptor family protein in merozites. Parasites were metabolically labeled with $^{35}$S-methionine/cysteine for 60 min., washed, and then chased in RPMI 1640 without additional metabolic label. Parasites were separated from culture supernatants by centrifugation and extracted in detergent (as indicated). Detergent extracts and culture supernatants were immunoprecipitated with anti-DR.1 sera (minutes of chase are shown over each lane).

Figure 9A:
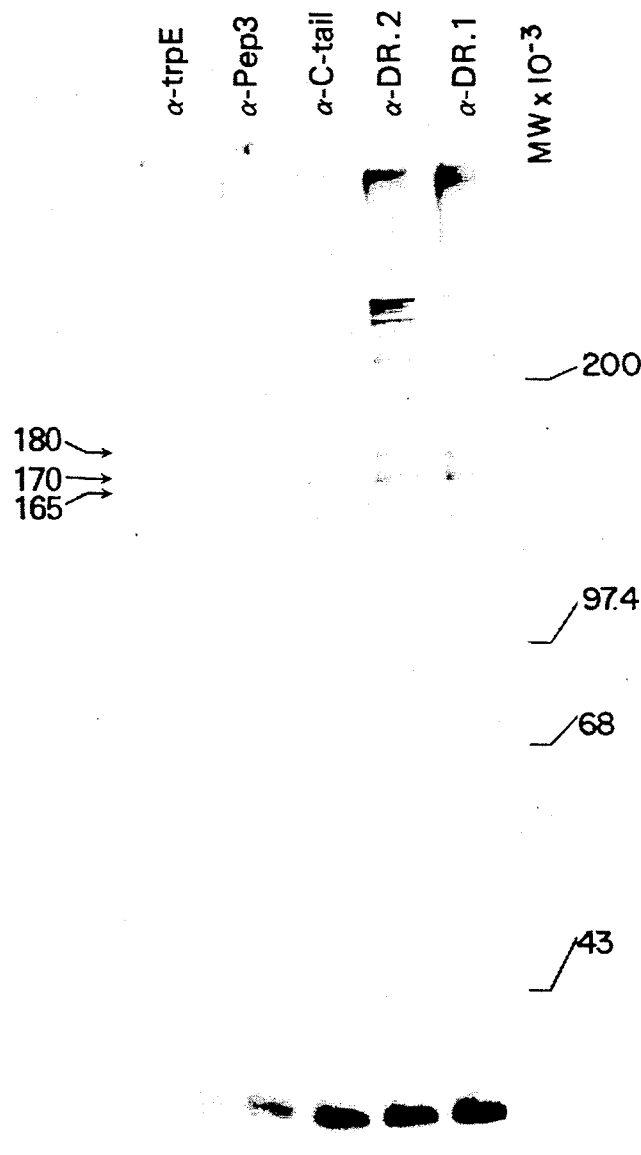

FIGS. 9A and B. In vitro translation of Duffy receptor gene family products and their inhibition with antisense oligonucleotides of pEco6. The molecular weight of the Duffy receptor precursors (arrow) were calculated relative prestained molecular weight markers (as marked for each gel) and the 135 kDa Duffy binding protein. (A) In vitro translation products of late schizont *P. knowlesi* RNA were immunoprecipitated with anti-DR.1, anti-DR.2, anti-C-terminus, anti-peptide 3, and anti-trp E. (B) In vitro translational was inhibited with oligonucleotide 31 (antisense) but not a complementary oligonucleotide 30.

FIGS. 10A to D. Immunofluorescent localization of the Duffy receptor family in schizonts.

Panels (B,D) show the immunofluorescence pattern, and panels (A,C) the corresponding phase contrast images. Free merozoites (cell #1) and fully-formed merozoites within mature schizonts (#2) show a discrete spot of fluorescence at their apical end. Less mature schizonts (#3) show diffuse apical florescence, and early schizonts (#4) show no staining above background (D).

FIGS. 11A to D. Immunoelectron microscopic localization of Duffy receptor family.

Duffy receptors are localized in micronemes (MN); Rhoptries (R) and dense granules (D) are not immune labelled. N indicates a nucleus. Bars equal to 0.2 μm.

Figure 12F:
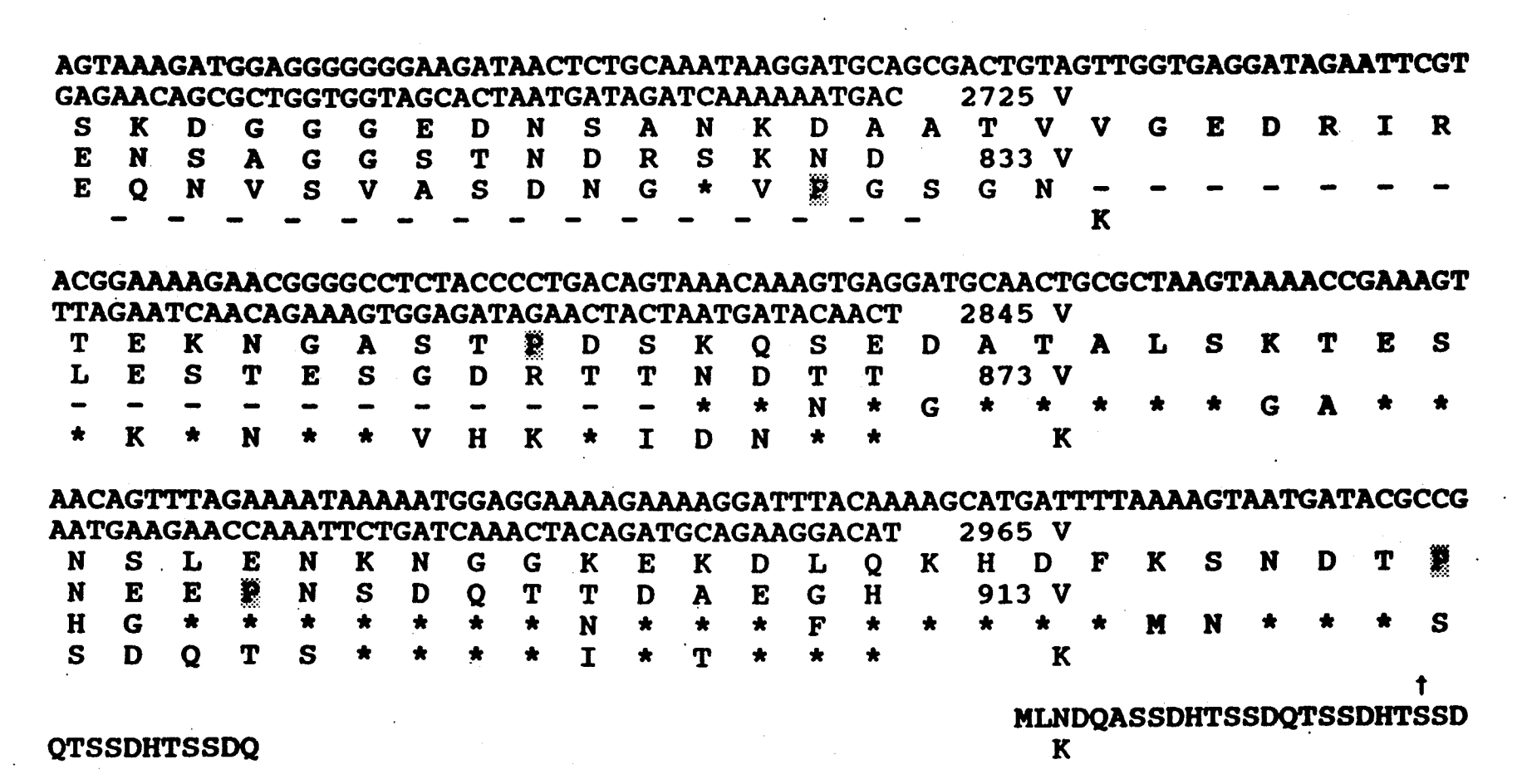

FIGS. 12A to I. Nucleotide sequence and deduced amino acid sequence of P. vivax Duffy receptor and a comparison of its predicted protein sequence with that of P. knowlesi.

The P. vivax Duffy receptor nucleotide sequence is shown on the upper line, amino acid sequence on the middle line and the amino acid sequence of P. knowlesi on the bottom line with asterisks indicating identity at the amino acid level. Spaces are inserted in P. knowlesi protein sequence for an optimal alignment. The repeated sequence (SSDHTSSDQT) of P. knowlesi is separated to another line for an optimal alignment. Cysteine residues are highlighted by reverse print and proline residues in a dashed box. The predicted signal peptide sequences of P. vivax is shaded and the transmembrane spanning hydrophobic sequence of P. vivax and P. knowlesi gene are lightly shaded. The beginning and end of the three introns are indicated below the nucleotide sequence. V: nucleotide or amino acid sequence of P. vivax Duffy receptor. K: amino acid sequence of P. knowlesi.

FIGS. 13A to D. Southern blot analysis of P. vivax genomic DNA.

P. vivax genomic DNA digests of DraI, EcoRI and HindIII were fractionated by agarose gel electrophoresis and then transferred to nylon membrane and hybridized with (A) pIC1 (B) pPvDR (C) 2.7 kb Hind III/EcoRI fragment of pPvDR, and (D) 1.4 kb Hind III/EcoRI fragment of pPvDR at 55° C. for 16 h. The filter was washed at a final stringency of 0.2 xSSC, 0.1% SDS at 55° C. for 60 min. The blot was stripped with 0.2M NaOH between hybridizations.

FIG. 14. Comparison of the introns between the P. vivax and the P. knowlesi genes.

The beginning and end of the three introns are indicated and the exon sequences are in bold type. Spaces are inserted in the sequences for a better alignment.

Figure 15:
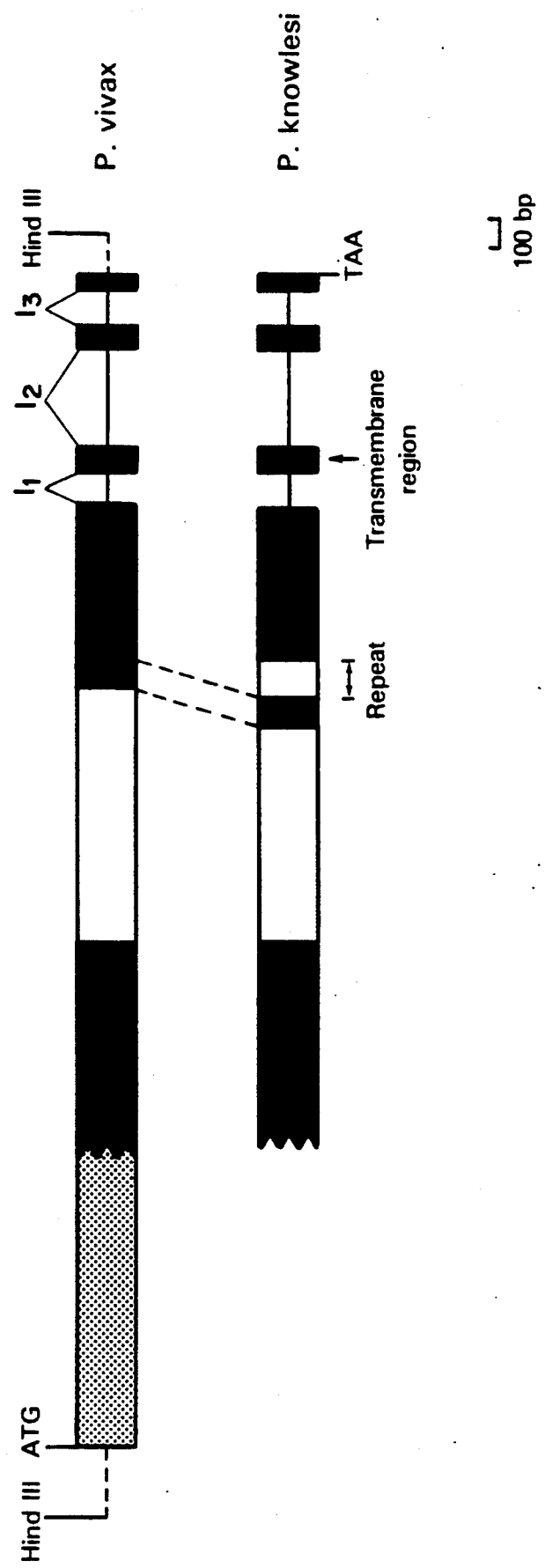

FIGS. 15. The structure of P. vivax Duffy receptor gene and its comparison with that of P. knowlesi.

Exons are shown as boxes, introns as solid lines, and 5' and 3' noncoding sequences as dashed lines. The homologous regions between P. vivax and P. knowlesi Duffy receptor gene are shown in black, and the nonhomologous region is shown as an open box. The amino terminal part in P. vivax is shown as stippled box because of unknown homology between the P. vivax and P. knowlesi genes in this region. Three introns ($I_1$, $I_2$ and $I_3$) and the transmembrane region are indicated. The start codon of the P. vivax gene, the stop codon, and the repeat region of P. knowlesi gene are marked on the figure.

FIG. 16A1 to C2. Comparison of the distributions of structurally important amino acid residues between P. vivax and P. knowlesi Duffy receptor gene.

(A) Cysteine residues (B) Proline residues (C) Aromatic residues (phenylalanine, tryptophan, and tyrosine). The plots of the amino acid residues were computed at intervals of 5 amino acids by using PRESIDUE program in PCGENE. The number of amino acids are shown on the X axis and the number of residues per interval of 5 amino acids are shown on the Y axis. The regions of homology and nonhomology are indicated on each figure (see FIG. 15).

Figure 17:
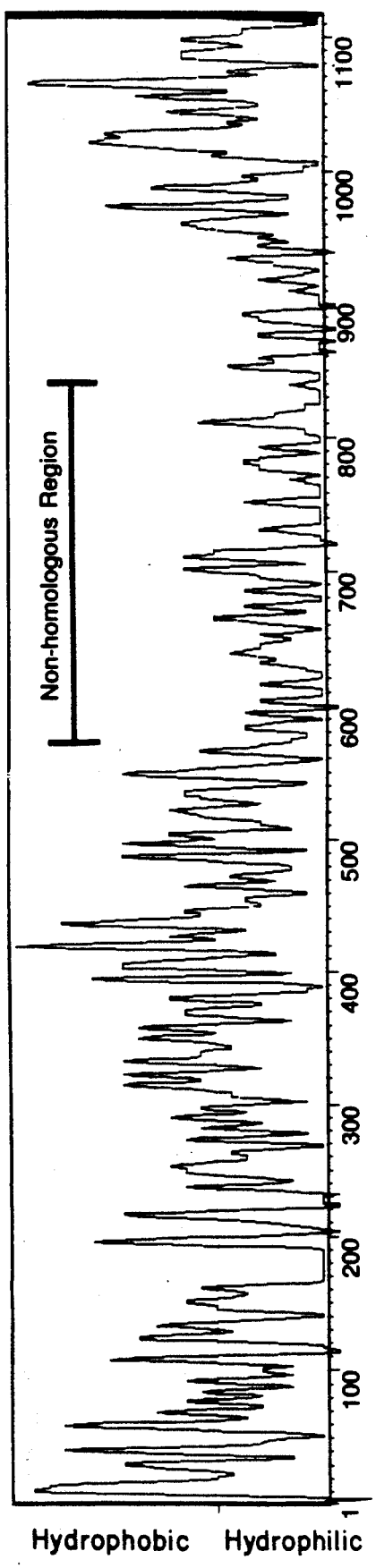

FIG. 17. Hydrophobicity profile of P. vivax Duffy receptor.

The plot of the hydrophobicity profile is computed by using NOVOTANY program in PCGENE. The amino acid number is shown on the X axis. The nonhomologous region is indicated.

DETAILED DESCRIPTION OF THE INVENTION

The present invention relates, in general, to a nucleic acid segment (e.g. a DNA segment) encoding all, or a unique portion, of a Duffy receptor of a Plasmodium parasite (particularly, Plasmodium knowlesi and Plasmodium vivax). A "unique portion" as used herein is defined as consisting of at least five (or six) amino acids or, correspondingly, at least 15 (or 18) nucleotides. The cloning and sequencing of the Duffy receptor gene family of P. knowlesi are described herein below. The P. vivax Duffy receptor gene was identified and cloned utilizing a probe from the P. knowlesi receptor gene family.

The present invention further relates to a DNA segment encoding a Duffy receptor of other Plasmodium parasites such as, for example, P. falcioarum. One of ordinary skill in the art, given the present disclosure, could easily identify and clone analogous genes in such species without undue experimentation.

In one embodiment, the present invention relates to a DNA segment encoding the entire amino acid sequence given in FIG. 1 or FIG. 12 (the specific DNA segments defined therein being only examples). The DNA segment can be genomic DNA or cDNA. DNA segments to which this invention relates also include those encoding substantially the same receptor as that of FIG. 1 or FIG. 12 which include, for example, allelic forms of the given amino acid sequences and alternatively spliced products.

The present invention also relates to a Plasmodium Duffy receptor protein separated from those proteins with which it is naturally associated. One skilled in the art can easily purify the Duffy receptor using methodologies well known in the art.

The present invention further relates to a recombinantly produced Duffy receptor with the amino acid sequence given in FIG. 1 or FIG. 12, an allelic variation thereof or a chimeric protein thereof. The present invention also relates to recombinantly produced unique peptide fragments of the Duffy receptor. Further, the present invention relates to a synthetic Duffy receptor protein or a unique synthetic peptide fragment thereof.

The present invention relates to a recombinant DNA molecule comprising a vector and a DNA segment encoding the Duffy receptor, or a unique portion thereof. Using methodology well known in the art, recombinant DNA molecules of the present invention can be constructed. Possible vectors for use in the present invention include, but are not limited to, eukaryotic vectors, pCDM8 and PRSV-NW. The DNA segment can be present in the vector operably linked to regulatory elements, including, for example, a promoter.

The invention further relates to host cells comprising the above-described recombinant DNA molecule. The recombinant DNA molecule may be stably transfected or transiently transfected into the host cell or infected into the host cell by a live attenuated virus. The host cells include prokaryotic cells, such as *Escherichia coli, Staphlococcus aureus,* and eukaryotic cells, such as *Sacchromvces cervisae, Spodptera frugiperda,* CHO and COS. Transformation with the recombinant molecules can be effected using methods well known in the art.

The present invention further relates to antibodies specific for the Duffy receptor of the present invention. One skilled in the art, using standard methodology, can raise antibodies (such as monoclonal, polyclonal, anti-idotypic and monoclonal catalytic [Sastry et al. PNAS 86:5728–5732 (1989)]) to the Duffy receptor, or a unique portion thereof. This is exemplified by the antiDR.1 serum and anti-DR.2 serum (described in the Examples below see "Production of antisera to fusion proteins and peptides").

The present invention also relates to a vaccine for use in humans against malaria. As is customary for vaccines, the Duffy receptor or unique portion thereof, can be delivered to a human in a pharmacologically acceptable vehicle. As one skilled in the art will understand, it is not necessary to use the entire protein. A unique portion of the protein (for example, a synthetic polypeptide corresponding to the Duffy receptor) can be used. Pharmacologically acceptable carriers commonly used in vaccines can be used to deliver the protein or peptide. Such carriers include MTP, tetanus toxoid or liposomes. Vaccines of the present invention can include effective amounts of immunological adjuvants known to enhance an immune response. Such adjuvants include IL-2 and alum.

The protein or polypeptide is present in the vaccine in an amount sufficient to induce an immune response against the antigenic protein and thus to protect against Plasmodium infection thereby protecting the human against malaria. Protective antibodies are usually best elicited by a series of 2–3 doses given about 2 to 3 weeks apart. The series can be repeated when concentrations of circulating antibodies in the human drops. Further, the vaccine can be used to immunize a human against other forms of malaria (that is, heterologous immunization).

The present invention further yet relates to receptor blocking therapy which disrupts the life cycle of the parasite in humans as with other infectious agents, e.g. [Byrn et al., Nature 344:667–670 (1990)]. Administering to a human antibodies of the present invention specific for the binding site of the Duffy receptor of the present invention can prevent invasion of red blood cells by the merozoite, a necessary event in the life cycle of the Plasmodium parasite. Alternatively, the Duffy receptor ligand (i.e., the Duffy blood group determinates) can be administered to a human. The receptor on the merozoite will bind the circulating ligand rather than the determinate on the red blood cells. Attachment of the merozoite to the red blood cells, and hence invasion of the parasite, is prevented.

EXAMPLES

For purposes of illustrating a preferred embodiment of the present invention the following non-limiting examples will be discussed in detail.

1. *Plasmodium Knowlesi* Duffy Receptor. Metabolically labeled parasites

*Plasmodium knowlesi* (Malayan H) schizont-infected erythrocytes ($2 \times 10^7$/ml) were metabolically labeled with 75 $\mu$Ci/ml [$^{35}$S]methionine/cysteine (ICN Radiochemicals) in methionine/-cysteine-deficient RPMI 1640 culture medium (30 mM HEPES, 0.2% dextrose, 5 mg/1 hypoxanthine, and 0.225% NaHCO), containing 2% foetal bovine serum or 50 $\mu$Ci/ml [$^{35}$S] methionine in methionine deficient RPMI 1640 culture medium. The parasites were cultured 9–11 hr. at 37° C. to allow complete rupture and release of merozoites. Culture supernatants were centrifuged at 20,000 g for 20 min before freezing at $-70^\circ$ C. [Haynes et al., J. Exp. Med. 167: 1873-1881 (1988)].

Erythrocyte binding assay

The erythrocyte binding assay was performed as described previously [Haynes et al., J. Exp. Med. 167: 1873–1881 (1988)]. Briefly, washed erythrocytes were incubated with culture supernatants (one volume of erythrocytes to four volumes culture supernatant), passed through silicone oil (GE Versilube F50), washed quickly in RPMI 1640, and passed through silicone oil again. For some experiments (see FIG. 7) the wash step was omitted to increase detection of the poorly absorbed proteins. Molecules absorbed onto the erythrocytes were eluted in a final concentration of 300 mM NaCl (20 $\mu$l of 1.5 M NaCl to 80 $\mu$l of packed erythrocytes). The eluted material was mixed 1:1 with SDS-PAGE sample buffer and electrophoresed.

Library screening

The 135 kDa Duffy binding protein was isolated from *P. knowlesi* culture supernatants by large-scale preparations of the erythrocyte binding assay using human Fy a−b+ erythrocytes. Eluted molecules were partially purified by SDS-PAGE, and electroblotted onto nitrocellulose. The position of the 135 kDa antigen was marked by immunolabelling the edges of each blot. Sera from an immune rhesus monkey [number 626, Miller et al., Exp. Parasitol. 41: 105–111 (1977)] was diluted to 1% in 0.05% Tween 20, phosphate-buffered saline (pH 7.4) (TPBS), and incubated with nitrocellulose strips of the 135 kDa protein. Strips were washed three times in TPBS. Bound antibodies were eluted in 100 mM glycine, 150 mM NaCl buffer (pH 2.8), then neutralized with 2 M tris (pH 8.0) and dialyzed with TPBS containing 0.05% NaN$_3$ [Torii et al., Infection and Immunity 57: 3230–3233 (1989)]. A size-selected (>800 bp) amplified *P. knowlesi* $\lambda$gt11 cDNA expression library was constructed from late schizont mRNA [Hudson et al., J. Mol. Biol. 203: 707–714 (1988)]. Recovered monospecific polyclonal antibodies to the 135 kDa Duffy binding protein and alkaline-phosphatase conjugated goat anti-human IgG (H+L) (Promega, cat. no. W3910) were used to screen the *P. knowlesi* $\lambda$gt11 cDNA library [Young et al., Proc. Natl. Acad. Sci, USA 80: 1194–1198 (1983)].

A genomic library was constructed in pUC 13 from EcoR I digested *P. knowlesi* (Clone A, Malayan H) DNA. Clones were selected by colony hybridization with oligonucleotide 13 (GGGGATCCGGGAACT-GATGAAAAGGCCAAG) using a final washing stringency of 48° C. in 6X SSC, 0.5% SDS for 20 min.

Subcloning and clone analysis

The $\lambda$gt11 cDNA clones, $\lambda$1C1 and $\lambda$2C1, were subcloned into plasmid vectors pUC 13 and Bluescript KS+, respectively. Plasmid was purified by conventional techniques from plasmid-transformed cells. Both strands of each clone were sequenced by the dideoxy termination method using synthetic oligonucleotide primers (Synthecell Corporation) and T7 DNA polymerase (US Biochemical) on denatured double-stranded DNA. *Plasmodium knowlesi* genomic DNA was prepared for pulse-field gel electrophoresis from schizontinfected rhesus erythrocytes using clones V1a nd V1c [Hudson et al., J Mol, Biol. 203: 707-714 (1988)].

Clone p1C1 has an insert of 2.6 kb with an open reading frame of 2.2 kb followed by 0.4 kb of untranslated region ending with a polyadenylation sequence at the 3' end. The sequence of p2C1 is identical to an internal region of p1C1 with the exception of one base. To determine if both sequences were present in genomic DNA, two 17 bp oligonucleotides which had the base from p2C1 or p1C1 in position 9 were used to probe restriction digests of *P. knowlesi* genomic DNA. The oligonucleotide probe from p1C1 hybridized to the three fragments in an EcoRI digest that were hybridized by the cDNA clones (see below). The probe from p2C1 did not hybridize at the same stringency, indicating the one bp difference in p2C1 was a cloning artifact or transcriptional error.

An oligonucleotide (oligo 13, FIG. 1) from the 5' end of the cDNA clone p1C1 hybridized only to a 6 kb EcoRI genomic fragment (FIG. 3C) and was used to clone this fragment (pEco6). From the 5' end pEco6 had sequence of 113 bp not present in p1C1 followed by sequence that was identical to p1C1 for the next 150 bp. Additional sequence unique to p1C1 and the 6 kb EcoRI genomic fragment was identified with oligonucleotide probes 46 and 52 (FIG. 4). At the 3' end of the open reading frame of pEco6, there were three introns identified as defined by genomic sequences that were not present in the cDNA sequences (FIG. 1). The 5' and 3' borders of the introns (GTA...YAG) were identical to consensus splice sites for other malaria and eukaryotic genes (Weber, 1988; Darnell et al., 1986). Comparison of internal restriction fragments (HaeIII and NdeI) indicated no additional introns or size differences between p1C1 and pEco6.

The deduced amino acid sequence of the C-terminal portion of the gene, which covered four exons (FIG. 1), shows that the gene has a 22 amino acid transmembrane segment followed by 45 amino acids at the C-terminus. The presence of a transmembrane domain is consistent with the function of a receptor molecule. Nine repeats of the pentapeptide SSD(Q/H)T occur 5' to the transmembrane segment. Two regions of high cysteine content are separated by a proline-rich region. There is no significant sequence identity of either the genomic or cDNA clones with any gene or protein in EMBL 21 or Swiss-Prot 13 databases, respectively (Intelligenetics).

Figure 2B:
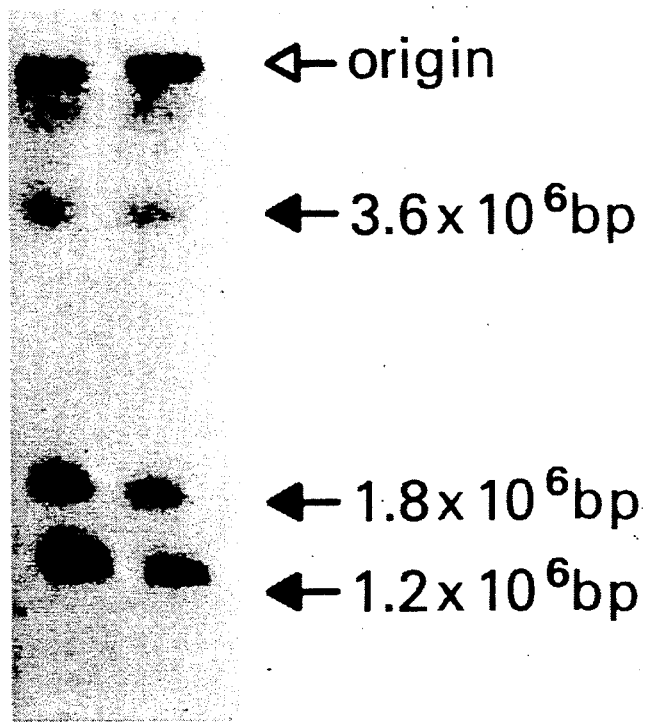

The cDNA clones p2C1 and p1 C1 hybridized with three chromosomes of 3.6, 1.8 and 1.2 Mb separated in a pulsed-field gel electrophoresis (FIG. 2), indicating three cross hybridizing elements in the *P. knowlesi* genome were recognized by the cDNA probe. Two subregions of p1C1 (DR.1 and DR.2, FIG. 1) were used to probe restriction digests of genomic DNA. The probes did not cross hybridize with each other. Probe DR.1 hybridized with three bands in EcoRI, NsiI, and NdeI digests (FIG. 3A). Probe DR.2 hybridized with bands of identical mobility to those hybridized with DR.1 in the EcoRI, NsiI, and NdeI digests plus three additional bands in the NdeI digest, including a 800 bp band known to be found in the DR.2 sequence (FIG. 3B). Hybridization with at least three bands in these digests is consistent with the hybridization to three chromosomes observed with the pulsed-field gel electrophoresis and suggests homology in the three gene fragments in both the 5'(DR.2) and 3'(DR.1) regions of p1 C1.

Southern blot analysis of the three cross hybridizing regions of *P. knowlesi* and *P. vivax* genomic DNA was performed with oligonucleotide probes from the sequence of pEco6 (FIG. 4). The probes hybridized with all three of the *P. knowlesi* EcoRI fragments at low stringency (see methods). At higher hybridization stringencies, some of the oligonucleotide probes hybridized to only one EcoRI restriction fragment (6 kb), two EcoRI restriction fragments (6 and 10 kb or 6 and 4 kb), or equally to all three EcoRI restriction fragments (FIG. 4). The failure of an oligonucleotide to hybridize to an EcoRI fragment was not due to the position of the EcoRI site because the oligonucleotide also did not hybridize with the corresponding fragments using other restriction enzymes. Furthermore, they did hybridize with all three EcoRI fragments at lower stringencies.

The analysis with oligonucleotide probes revealed that the 5' ends of the homologous *P. knowlesi* genes are divergent. In the 5' portion of pEco6 only 1 of 5 oligonucleotide probes hybridized at high stringency with the 4 kb EcoRI fragment and 3 of 5 hybridized with the 10 kb EcoRI fragment, but 4 of 4 hybridized with *P. vivax* genomic DNA (FIG. 4). These data are consistent with the fact that the 6kb EcoRI fragment is most similar to the equivalent single copy Duffy receptor gene present in the *P. vivax* genome (Fang et al., unpublished data). The oligonucleotides from the central region (50, 52 and 54) were not hybridized to *P. vivax* because the sequence of the *P. vivax* Duffy receptor is non-homologous in this region (Fang et al., unpublished data). In the 3' region of the gene (oligonucleotides 56 to 35; FIG. 4), there was a high degree of homology among the three *P. knowlesi* genes.

RNA purification and analysis

White blood cells were removed from the parasitized blood using a Sepacell R-500 cartridge (Baxter Healthcare), late-stage schizonts of *P. knowlesi* were isolated by centrifugation on 45% Percoll (Pharmacia) gradients, and cultured 3-4 hr in RPMI 1640 culture medium with 50 μg/ml chymostatin and 50 μg/ml leupeptin. The RNA was extracted by a single step method using 4 M guanidinium thiocyanate, 25 mM sodium citrate, pH 7, 0.5% sarcosyl, and 100 mM β-mercaptoethanol (Chomczynski and Sacchi, 1987)(RNAzol, Cinna/Biotecx).

For Northern blot analysis the RNA from the fifth preparation was enriched for the polyA fraction twice purified over oligo(dT)-cellulose spun columns (Pharmacia). The polyA enriched RNA (1 μg per lane) was separated by agarose gel electrophoresis (1% agarose, 20 mM MOPS, 5 mM sodium acetate, 0.5 mM EDTA, 200mM formalin, 0.5 μg/ml ethidium bromide), washed 2 hr in several changes of DEPC-treated distilled water, equilibrated in 20×SSC, transferred onto GeneScreen Plus (DuPont), crosslinked onto the membrane with ultraviolet (Stratagene), and dried under vacuum (modified from standard procedures of Maniatis et al., 1982). Northern blots were hybridized with the p1C1 insert (see FIG. 5) and oligonucleotides (111, CTTTGTCTATTGATCATCTTTT; 112, TTAATCTAGCTTCCACTCTAAT; 113, AAGGAATAATGCAGAATGGTGT; 60, GAAGCTCCACAGATATTGAGCACA) using the same procedures described above for Southern blots.

In vitro translations of mRNA were performed with rabbit reticulocyte lysate according to manufacturer's recommendations (Promega Biotech) with 5 μg total RNA. The in vitro translated products were immunoprecipitated as described below. Hybrid arrest of in vitro translation was performed as described previously (Pines and Hunt, 1987) with sense (oligo 30: ATG-GGAACTAATATGGA) and antisense (oligo 31: TCCATATTAGTTCCCAT) oligodeoxynucleotides (Synthecell Corporation). Ten 10 ng oligodeoxynucleotide (1 µl in DW) combined with 5 µg total RNA (5 µl in 10 mM HEPES), incubated at 37° C. for 20 min, and treated with 1U RNase H (1 µl in 10 mM tris (pH 7.5), 50 mM KCl, 5 mM MgCl$_2$, 0.05 mM DTT, 25 µg BSA, and 25% glycerol)(Bethesda Research Laboratories) for 30 min at 37° C. before in vitro translation as above.

Two transcripts of 3.8 and 4.2 kb were identified by Northern blot analysis using p1C1 as a probe (FIG. 5). To determine whether the different RNA species of P. knowlesi were products of alternative splicing of a single gene or transcripts of different genes we used various oligonucleotides to probe Northern blots. Oligonucleotides probes from the three introns did not hybridize to Northern blots but did hybridize to the 6 kb EcoRI fragment on Southern blots. An oligonucleotide probe overlapping the possible splice site between the first and fourth exon also did not hybridize to a Northern blot of P. knowlesi polyA RNA. The data indicate that the two transcripts originated from two genes and not from alternative splicing of a single gene.

Production of antisera to fusion proteins and peptides.

Nonoverlapping fragments DR.1 and DR.2 were created by polymerase chain reaction (PCR) using oligonucleotide primers derived from the sequence of p1C1 (see FIG. 1). Each PCR fragment was constructed with a 5' BamHI restriction site in frame with the pATH2 vector (pJH12) trp E open reading frame [Spindler et al., J. Virol. 49: 132–141 (1984)], provided by T. J. Koerner) and multiple stop codons ending with a SalI restriction site at the 3' end (DR.1 5' oligonucleotide primer: CCGGGGATCCGCAAAATGAGGGT-GCAACTGCG; DR.1 3' oligonucleotide primer: TTTTGTCGACCCGAACCGTT-CATATACTTCTC; DR.2 5' oligonucleotide primer: GGGGATCCGGGAACTGATGAAAAGG-CCAAG; DR.2 3' oligonucleotide primer:GGGGTCGACTTATTAATTGCCAGATC-CAGGAACATT).

The PCR was run for 30 cycles of 92° C. for 1 min., 45° C. for 1 min., and 74° C. for 4 min. (plus 4 sec. added each cycle). Each PCR reaction was purified by phenol/chloroform and ethanol precipitation, digested with BamHI and SalI, purified by agarose gel electrophoresis, isolated on glass powder, and ligated to pATH2. Escherichia coli strain RR1 was transformed with pATH2/DR.1 or pATH2/DR.2. Liquid cultures of each clone were induced to produce trp E fusion proteins by the addition indole acrylic acid (10 µg/ml) and the cells were grown until saturation. Cells expressing fusion proteins were recovered by centrifugation 20 min. at 5000 g, resuspended in 10 ml of 0.3 M NaCl, 0.5 mM EDTA, 50 mM tris, pH 7.4 (TEN) containing 1 mg/ml lysozyme and incubated 15 min. on ice. After addition of 0.5 ml of 4% Triton X-100 (10 min, on ice) the solution was mixed with 12 ml of 1.5 M NaCl, 12 mM MgCl, containing 23 µl of 20 mg/ml DNase and incubated 60 min. at 4° C. Insoluble material was pelleted by centrifugation at 4000 g for 15 min. and washed three times in TEN buffer. Triton X-100 insoluble pellets containing fusion proteins of DR.1 (80 kDa) and DR,2 (100 kDa) were separated by SDS-PAGE. The fusion proteins were electroeluted (Bio-Rad model 422 Electro-Eluter) from gel slices into 25 mM tris (pH 8.3), 192 mM glycine, 0.1% SDS. The electrocuted fusion proteins were emulsified with *Freund's complete adjuvant for primary immunizations and incomplete adjuvant for each booster immunization.

The C-terminal peptide (DIEHMQQFTPLDYS) and peptide 3 (EGKSSTNEADPGSQSGAPASRS) (7.5 µg purified by HPLC) were conjugated to KLH (Calbiochem, cat. no. 374805)(7.5 µg) overnight at room temperature in 7.5 ml of PBS using 940 µl of 0.05% glutaraldehyde. Conjugated proteins were dialyzed 24 hr with 500 volumes of PBS. Rabbits were immunized with conjugated proteins: primary immunizations were emulsified in Freund's complete adjuvant and boosting immunizations were emulsified in incomplete adjuvant.

Erythrocyte preadsorptions and immunoprecipitations

Culture supernatants were incubated with erythrocytes from various hosts to remove the molecules that bound to these erythrocytes (see Table I below). Culture supernatant was incubated twice for 30 min with packed erythrocytes at a ratio of 0.5 ml packed erythrocytes per ml of culture supernatants or at a ratio of 1 ml packed erythrocytes per 1 ml of culture supernatants. Immunoprecipitations were modified from techniques described previously [David et al, Mol. Biochem. Parasitol. 11: 267–282 (1984)]. Parasite extracts were made from $1\times10^9$ cultured schizonts extracted in 3 ml of 1% Triton X-100 in 10 mM HEPES, pH 8.5, 50 µg/ml chymostatin, and 50 µg/ml leupeptin, and centrifuged 20 min at 20,000 g. Culture supernatants and detergent extracts (400 µl each) were incubated 30 min with 5 µl anti-DR.1 serum (see FIG. 4A and 4B) and anti-DR.2 serum (see FIG. 3C), then 75 µl of a 50% suspension of protein A Sepharose CL-4B (Pharmacia) was added and incubated another 30 min, washed once with 0.5% bovine serum albumin in 0.5% Triton X100, 0.15 M NaCl 1 mM EDTA, 50 mM tris, pH 7.4 (NETT), once in NETT, once in NETT with 0.5 M NaCl, twice in NETT, and separated by SDS-PAGE. To help separate the closely migrating proteins of interest, SDS-PAGE was performed according to the Laemmli method using 0.6% instead of 0.8% bisacrylamide in a total of 30.0% acrylamide monomer and a mixed-chain length SDS preparation (69% lauryl, 24% myristyl, 5% cetyl sulfate salts; Sigma, cat. no. L-5750) in SDS-PAGE electrophoresis buffers [Margulies et al. Anal. Biochem. 136: 309–313 (1984)]. All SDS-PAGE gels contained a final concentration of 7.5% acrylamide monomer and were either 1.5 mm or 0.75 mm thick. The SDS-PAGE gel (see FIG. 4A) contained 0.6% bis crosslinker and mixed-length SDS or (see FIG. 3C) contained 0.8% bis crosslinker and pure SDS.

The antisera raised to portions of the cloned gene immunoprecipitated erythrocyte binding proteins of P. knowlesi. These soluble proteins are divided into two groups: 1) proteins of 135 kDa and 120 kDa that bind to human Duffy positive erythrocytes and rhesus erythrocytes and 2) those that do not bind human erythrocytes but bind to rhesus erythrocytes.

Antisera to fusion proteins of non-overlapping regions of the Duffy receptor (DR.1 and DR.2) immunoprecipitated the 135 kDa duffy binding protein from culture supernatants. The immunoprecipitated 135 kDa protein was removed by preadsorption with Duffy b human erythrocytes, but not by Duffy negative erythrocytes (FIGS. 6, 7, and Table I). The immunoprecipitated 135 kDa protein was also absorbed by erythrocytes of Old World (rhesus) and New World (Aotus and Cebus) monkeys which are Duffy positive. The 120 kDa Duffy binding protein was precipitated by anti-DR.1 (FIGS. 6, 7) and by anti-peptide 3 serum but not by anti-DR.2 serum. The fact that antisera to different regions of p1C1 immunoprecipitated the 135 kDa and the 120 kDa Duffy binding proteins indicates that the clone encodes the Duffy receptor or a member of the Duffy receptor family.

The DR.1 and DR.2 antisera also immunoprecipitated soluble proteins from *P. knowlesi* culture supernatants that bound to rhesus erythrocytes but not to human erythrocytes. A 138 kDa protein, which was adsorbed only by rhesus erythrocytes, was immunoprecipitated by both anti-DR.1 and anti-DR.2 sera (FIG. 7). Proteins of 125 and 160 kDa, which were also specifically adsorbed by rhesus erythrocytes were only immunoprecipitated by anti-DR.1 sera (FIGS. 6, 7). A 155 kDa protein which was adsorbed by Aotus erythrocytes and partially adsorbed by rhesus erythrocytes (Miller et al., 1988) was immunoprecipitated by both anti-DR.1 and anti-DR.2 sera. In some preparations a 153 kDa protein that was not adsorbed by any erythrocyte in our assay was immunoprecipitated by both DR.1 and DR.2 antiserum.

The antiserum to the C-terminal peptide did not immunoprecipitate any of the soluble erythrocyte binding proteins, but it did immunoprecipitate the membrane-bound proteins and the proteins from in vitro translated mRNA that were seen by the anti-fusion protein sera (see below). As the C-terminus is 44 amino acids from the putative transmembrane domain, the failure of this antisera to immunoprecipitate the soluble proteins is consistent with the proteolytic cleavage site for the soluble proteins being located amino to the transmembrane domain.

diately in boiling SDS. Samples denatured in SDS were boiled 5 min in 0.5% SDS, 50 mM tris, pH 7.4, 100 mM NaCl, and 2 mM EDTA, cooled, mixed with protease inhibitors (0.5 mM PMSF, 1 mM TLCK, 1 mM TPCK, 50 $\mu$g/ml chymostatin, and 50 $\mu$g/ml leupeptin), and frozen to $-70°$ C. When used these rapidly denatured samples were boiled again, fresh protease inhibitors were added along with 10 $\mu$g/ml DNase I and 10 mM MgCl$_2$, mixed with Triton X-100 to a final concentration of 2% and used in immunoprecipitations.

The results are shown in FIG. 8. All immunoprecipitations shown were done with anti-DR-1. In (A), the pellets were extracted in Triton X-100 (1% Triton X-100 in 10 mM HEPES, pH 8.5, 50 $\mu$g/ml chymostatin, and 50 $\mu$g/ml leupeptin). (B) shows supernatants from the cultures used for the Triton X-100 pellets. In (C), the pellets were extracted by boiling in SDS (0.5% SDS, 50 mM tris, pH 7.4, 100 mM Nacl, and 2 mM EDTA), cooled and then mixed with protease inhibitors. (D) shows supernatants from the cultures used for the SDS-extracted pellets. The supernatants in (B) and (D) were first mixed with SDS (to 0.5%) and then Triton X-100 (to 2%) before immunoprecipitation. Erythrocyte binding assays were done using supernatants from 9 hour cultures and were run in the right-hand lanes of (B) and (D).

Membrane-bound precursors to the soluble Duffy receptor family proteins were immunoprecipitated from detergent-solubilized parasites. From Triton X-100 extracted parasites, anti-DR.1, anti-DR.2 and anti-C-terminus sera immunoprecipitated a closely migrating doublet of 148 and 145 kDa and a minor protein of 170 kDa (FIG. 8). The question of whether the 145 kDa protein was a proteolytic product of the 148 kDa protein was determined by pulse-chase experiments. During the chase period, the intensity of both the 148 and 145 kDa (FIG. 8A) decreased at a similar rate and two soluble proteins of 138 and 135 kDa appeared (FIG. 8B), which are the rhesus and Duffy binding proteins, respectively. Since it is possible that the 148/145 kDa doublet might have been an artifact of proteolytic

TABLE I

| Soluble protein (kDa) | Soluble erythrocytes binding proteins from *P. knowlesi* culture supernatants. | | | | | | | |
|---|---|---|---|---|---|---|---|---|
| | ERYTHROCYTE BINDING SPECIFICITY[A] | | | | PRECIPITATING ANTISERA[B] | | | |
| | Human Duffy Pos. | Human Duffy Neg. | Rhesus | Aotus | $\alpha$-DR.1 | $\alpha$-DR.2 | $\alpha$-C-terminal peptide | $\alpha$-Peptide 3 |
| 120 | + | − | + | + | + | − | − | + |
| 125 | − | − | + | − | + | − | − | − |
| 135 | + | − | + | + | + | + | − | − |
| 138 | − | − | + | − | + | + | − | − |
| 155 | − | − | + | + | + | + | − | − |
| 160 | − | − | + | − | + | − | − | − |

[A] +  adsorbs, −  does not adsorb;
[B] +  immunoprecipitated, −  not immunoprecipitated; the location of DR.1, DR.2, and the peptides are described in FIG. 1.

Pulse-chase analysis

*Plasmodium knowlesi* cultures were incubated 1 hr with 150 $\mu$Ci of $^{35}$S-methionine/cysteine (ICN Radiochemicals), 50 $\mu$g/ml of chymostatin, and 50 $\mu$g/ml leupeptin in RPMI 1640 culture medium, washed two times in culture medium, separated into 5 aliquots ($2 \times 10^8$ schizonts each) and cultured for 0, 90, 180, 270, (see FIG. 8A and 8B) and 360 min or 0, 30, 60, 90, and 540 min (see FIG. 8C and 8D). At each time point an aliquot was centrifuged for 5 min at 1000 g. Supernatants and pellets were separated. Pellets were then either frozen immediately to $-70°$ C. or denatured immediately cleavage during Triton X-100 extraction (David et al., 1984), the pulse-chase experiments were repeated and the parasites were extracted in boiling SDS. The 148/145 kDa doublet in the SDS extraction (FIG. 8C) was similar to that found in the Triton X-100 extraction during the pulse-chase periods. Immunoprecipitation and hybrid arrest of in vitro translated mRNA The primary translation products of the Duffy receptor gene family were identified by immunoprecipitation of proteins translated in vitro from parasite mRNA. The three antisera (anti-DR.1, anti-DR.2 and anti-C-terminus peptide) immunoprecipitated a set of three proteins of 180 kDa, 170 kDa and 165 kDa from five different RNA preparations (FIGS. 9A). The 180 kDa band was always the most intense whereas the intensity of the 170 and 165 kDa bands varied with the RNA preparation. Other proteins present in the anti-DR.2 immunoprecipitate were not present in the anti-DR.1 or the anti-C-terminus peptide immunoprecipitate, indicating that these were nonspecific. Proteins of 140 kDa that were present in the immunoprecipitates from immune sera were also immunoprecipitated by some sera from non-immunized rabbits. Further evidence that the 140 kDa immunoprecipitates was unrelated to the Duffy receptor was its absence from the in vitro translations of mRNA from those parasites with a mutation in the 140 kDa gene (Hudson et al., 1988).

Figure 9B:
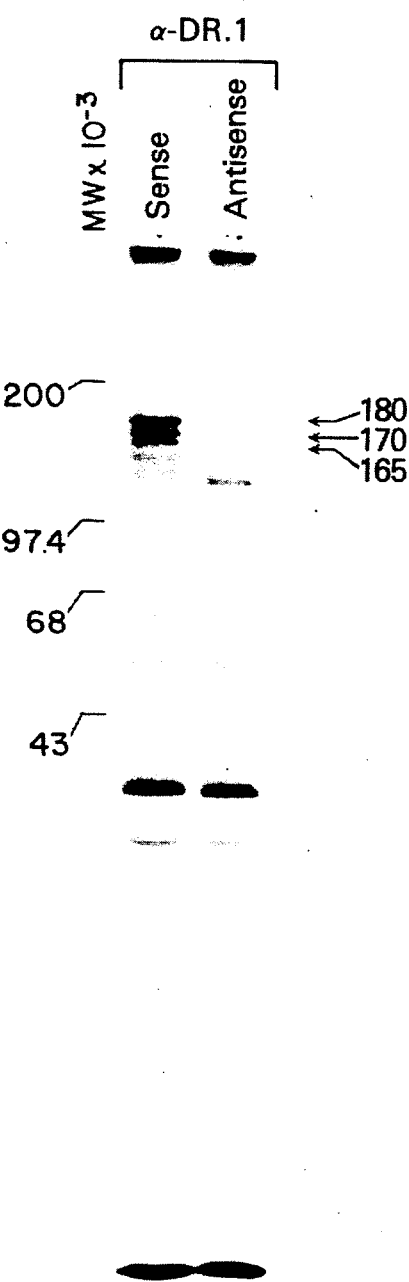
Figure 10A:
Figure 10B:
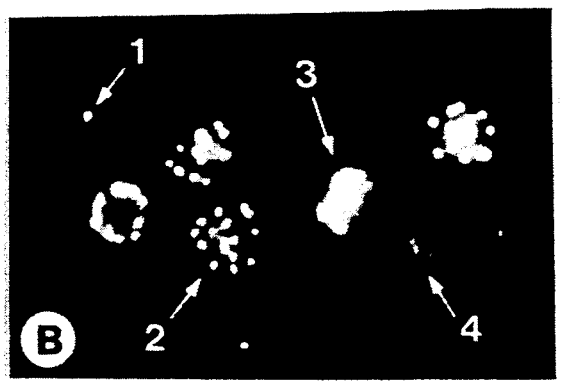
Figure 10C:
Figure 10D:
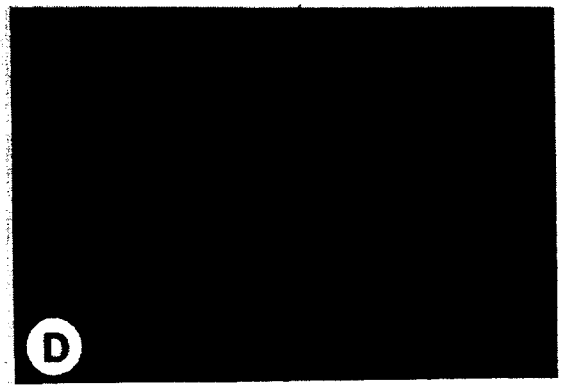

Antisense oligonucleotides complimentary to sequence of the 5' end of pEco6 blocked in vitro translation of all three products of 180, 170 and 165 kDa (FIG. 9B), The inhibition of in vitro translation of these three proteins was specific for the following reasons. First, the sense oligonucleotide did not block synthesis of the three proteins (FIG. 9B). Second, the higher molecular weight bands seen in immunoprecipitates with anti-DR.2 (FIG. 9A) were unaffected by the antisense oligonucleotide. Third, the total incorporated $^{35}$S-methionine TCA precipitable counts were the same for samples with and without the antisense oligonucleotide.

The data indicate a family of genes are expressed that yield a family of erythrocyte binding proteins, at least one of which is a Duffy binding protein. We refer to this family of erythrocyte binding proteins and their membrane-bound precursors as the Duffy receptor family.

Immunofluorescence microscopy

All incubations were at 23° C. Thin films of cultured P. knowlesi schizonts on glass slides were air-dried and fixed 5 min in PBS containing 1% formaldehyde. The fixed samples were rinsed in PBS and incubated 5 min in block buffer (PBS containing 0.1% Triton X-100 and 2.5 mg/ml normal goat serum). The slides were then incubated 60 min in a humidified chamber with immune or non-immune serum diluted 200-fold in block buffer, washed with block buffer (3 times, 5 min each), and incubated 30 min with rhodamine-conjugated goat anti-rabbit IgG (Southern Biotechnology Associates, Inc.) diluted 250-fold in block buffer. Slides were washed with block bufffer (3 times, 5 min each), mounted in 90% glycerol, 10 mM Tris pH 7.4, and viewed on a Zeiss Axiophot fluorescence microscope.

Antisera to the Duffy receptor family proteins permitted the study of their localization in fixed, detergent-permeabilized schizontinfected erythrocytes and merozoites (FIG. 10). These proteins were first detectable late in schizont development; a diffuse fluorescence developed at the apical end of developing merozoites at the 8+nuclei stage of schizonts (FIG. 10B). Strong discrete fluorescence appeared at the apical end when the merozoites were fully formed. At this stage the hemozoin pigment had coalesced into a single refractile granule, an event that occurs just before rupture. A strong spot of fluorescence was also seen at the apical end of free merozoites. Control antisera showed only faint background staining of infected cells (FIG. 10D). Only fixed and permeabilized parasites showed positive immunofluorescence; the Duffy receptor family proteins were not found on the surface of intact, invasive merozoites.

Immunoelectron Microscopy

Samples were prepared for immunoelectron microscopy by fixation in 1% formalin and 20 mM ethyl acetimidate HCl (Geiger et al., 1981)(EAI; Serva Feinbiochemica 11175) for 5 min in RPMI 1640 culture medium followed by the addition of either 8% glutaraldehyde to a final concentration of 0.1% for 15 min or 100 mM ethylene glycolbis (succinimidylsuccinate) (EGS; Pierce 21565) at room temperature or 37° C. for 30 min then washed and stored in RPMI 1640 with culture additives and 0.1% NaN$_3$. Other samples were fixed with 1% formalin in PBS only for 1 hr at room temperature then washed and stored in PBS with NaN, until embedded. Glutaraldehyde as the only fixative destroyed reactivity with all antisera. All samples were dehydrated, embedded in LR White and probed with antibody as described previously [Torii et al., Infection and Immunity 57: 3230–3233 (1989)] (see FIG. 11A-C).

The ferritin-bridge procedure was modified from that described previously [Willingham, Histochem. J. 12; 419–434 (1980)]. Specimens were fixed in 1% formalin in PBS for 1 hr at room temperature and washed three times in pBS with 200 mM NaCl (350 mM NaCl total), 0.1% Triton X-100. The buffer in all subsequent steps contained 200 mM NaCl, 1 mM EDTA, 2.5 mg/ml goat serum (Jackson Laboratories, cat. no. 005–000–121) added to PBS (pH 7.4). Fixed samples were incubated 1 hr at 4° C. in each of the following antibody solutions followed by 6 quick rinses and a 30 min wash. 1) primary antibody—rabbit sera, anti-DR.1 and anti-DR.2, were each diluted 1:200 in the washing buffer. 2) secondary antibody—2.2 mg/ml affinity-purified goat anti-rabbit IgG (Jackson Laboratories, cat. no. 111–00–5–003). 3) tertiary antibody—2.3 mg/ml affinity-purified rabbit anti-horse ferritin (Jackson Laboratories, cat. no. 308–005–063); 4) electron-dense label—200 μg/ml horse spleen ferritin (Sigma Chemical, cat. no. Co. F-4503). Samples were then fixed overnight at 4° C. in 0.1% glutaraldehyde in PBS containing 200 mM NaCl and 0.1% Triton X-100, washed in PBS containing 0.05% NaN,, post-fixed in 1% osmium tetroxide, dehydrated, and embedded in Epon 812 (see FIG. 8).

The precise location of the Duffy receptor family was determined by immunoelectron microscopy. The Duffy receptor family is localized in the micronemes of late schizonts and free merozoites (FIG. 11). This same localization was found with anti-DR.1, anti-DR.2 and anti-C-terminus sera, and was independently confirmed by the ferritin-bridge technique using anti-DR.1 and anti-DR.2 sera (FIG. 11D). No detectable immunolabelling of merozoites was seen using control antisera.

2. *Plasmodium* vivax Duffy Receptor

Genomic DNA Extraction

The Salvador I strain of P. vivax was grown in a chimpanzee [Collins et al., J. Parasitol. 59: 606–608 (1973)]. The genomic DNA of P. vivax was extracted as follows. Parasitized blood was collected in anticoagulant citrate phosphate dextrose (Fenwal, Deerfield, Il.), filtered through a Sepacell R500A leukocyte removal unit (Baxter, Columbia, Md.) to remove leukocytes and then was passed over a column of acid-treated glass beads (Thomas Scientific, Swedesboro, N.J.) to remove platelets. The parasitized cells were centrifuged at 2000 ×g for 10 min at room temperature and washed twice with phosphate-buffered saline (PBS), pH 7.4. The cells were resuspended in an equal volume of 0.15% saponin in PBS and incubated at 37° C. for 10 min. Two volumes of PBS were added, and the cells were centrifuged again and washed once with PBS. The cells were then lysed at 37° C. in 10 mM Tris, pH8.0, 10 mM EDTA, 10 mM NaCl, 2% SDS, and 100 µg/ml proteinase K. The lysate was extracted with phenol, then chloroform, RNAse treated, reextracted with phenol, then chloroform, ethanol precipitated and adjusted to a final concentration of 1 µl in 10 mM Tris, pH 8.0, 1 mM EDTA.

Library Construction and Colony Screening

Five µg of P. vivax genomic DNA were digested with Hind III (BRL, Gaithersburg, Md.) at a concentration of 1 unit/µg for 2 h at 37° C. The DNA fragments were fractionated by agarose gel electrophoresis and DNA fragments of 3-5 kb were isolated from the gel on glass (GeneClean kit BIO 101, La Jolla, Calif.). Eluted DNA fragments (500 ng) were ligated to HindIII digested, phosphatase-treated pUC 13 vector DNA (200 ng, Pharmacia, Piscataway, N.J.) and used to transform competent DH 5α cells (BRL). Filter lifts of 6000 colonies were screened with a 2.7 kb cDNA clone (p1C1) of P. knowlesi gene (Adams et al., unpublished data) by hybridization in 1 M NaCl, 1% SDS, 50 mM Tris pH 8.0, and 200 µg/ml heparin at 55° C. for 16 h. The filters were washed at a final stringency of 0.2 ×SSC, 0.1% SDS for 1 h at 55° C. Autoradiography at −70° C. for 12 h was sufficient to identify a positive colony, pPvDR.

DNA Sequencing

Restriction fragments of pPvDR were subcloned into pBluescript-SK II (Stratagene, La Jolla, Calif.) and single-stranded DNA was prepared as described [Dente et al., Nucleic Acids Res. 11, 1645-1655 (1983)] except pBluescript-SK II (Stratagene, La Jolla, Calif.) was used as the plasmid and M13K07 used as the helper phage (Promega, Madison, Wis.). DNA was sequenced by the dideoxynucleotide terminator method (USB Sequenase version 2.0 kit, Cleveland, Ohio) using universal sequencing primers and oligonucleotides from known sequences. Greater than 90% of the sequence was determined from both strands. Computer-assisted sequence analysis and comparison were performed using PCGENE (Release 6.01, Intelligenetics), Polymerase Chain Reaction (PCR)

The nonhomologous region was amplified by pCR using 10 ng of ppvDR, a 5′ primer (FIG. 12, nucleotide 2129 to 2149 plus a BamHI site at its 5′ end: ggggatc-cAGTGATATTGCCGAAAGTGTA) and a 3′ primer (FIG. 12, inverted and complementary sequence from pPvDR nucleotide 2729 to 2749 plus a HindIII site at its 5′ end: ataagcttG-GTAGAGGCCCCGTTCTTTTC). The reaction mixture contained 100 mM Tris-HCl, pH 8.3, 500 mM KCl, 15 mM MgCl$_2$, 0.01% gelatin (Sigma, St. Louis, Mo.), 0.2 mM dNTPs each, 600 ng of each primer, 2.5 U Taq DNA polymerase (Cetus, Norwalk, Conn.), in a final volume of 100 µl, overlaid with 100 µl of mineral oil (Fisher Scientific, Fair lawn, N.J.) and was subjected to 30 cycles of amplification in a Perkin-Cetus thermal cycler. Thermal cycling conditions Were 1 min at 94° C., 1 min at 42° C., and 1 min at 72° C. The 200 bp PCR product was purified from 0.8% agarose gel, labelled. with $^{32}$P-dATP (BRL random priming kit) to $10^9$ cpm/µg, and used as a probe to hybridize with P. know-lesi genomic DNA restriction digest under the conditions described below.

Southern Blot Analysis

P. vivax genomic DNA was digested with DraI, EcoRI, and HindIII, and P. knowlesi genomic DNA with DraI and EcoRI under the conditions recommended by the manufacture (BRL). Restriction fragments were fractionated by agarose gel electrophoresis and transferred to GeneScreen Plus membranes (NEN, Boston, Mass.) as previously described [Kaslow et al., Mol. Biochem. Parasitol. 33: 283-288 (1989)]. The P. vivax filter was hybridized with (1) 0.05 µg $^{32}$p-plCl DNA; (2) 0.5 µg $^{32}$p-pPvDR DNA; and (3) 0.05 µg $^{32}$p-Hind III/EcoR I fragments (2.7 and 1.4 kb) of pPvDR DNA, and the P. knowlesi filter with 0.05 µg $^{32}$p-PCR product of P. vivax for 16 h at 55° C., Unbound label was removed by two washes in 2 ×SSC, 0.5% SDS at room temperature for 15 min, followed by one wash in 0.2 ×SSC, 0.1% SDS at 55° C. for 60 min. Hybridizations were visualized by autoradiography at −70° C.

Cloning of P. vivax Duffy Receptor Gene

A 2.7 kb cDNA clone of the P. knowlesi Duffy receptor gene family, p1C1, was used as a hybridization probe in Southern blot analysis of P. vivax genomic DNA (FIG. 13A). p1C1 hybridized to a HindIII fragment (4.1 kb), two EcoRI fragments (3.8 and 2.3 kb), and DraI fragments of 2.7 kb and 150-300 bp. A size-selected (3-5 kb) HindIII genomic DNA library of P. vivax was constructed in pUC 13 and screened with p1C1. A 4.1 kb HindIII fragment was cloned and named pPvDR.

Characterization of the P. vivax Duffy Receptor Gene and Sequence Comparison with P. knowlesi The P. vivax sequence was determined by using the dideoxynucleotide terminator method. Translation of the P. vivax gene most likely begins at the ATG at nucleotide position 228-230 because this ATG is followed by a typical eukaryotic signal sequence (FIG. 12). The sequence consists of positively-charged amino acids, a hydrophobic region of 12 amino acids and a signal between amino acid 22 and 23 that fits the eukaryotic consensus for cleavage. The cleavage site had a value of 6.74, as determined by using PSIGNAL program in PCGENE with 6.0 as the cut off value. Although the open reading frame from genomic DNA ends at nucleotide 3414, the mature mRNA is likely to be formed by the removal of introns and the splicing of exons. The reasons for predicting the presence of introns in the P. vivax gene were as follows. The P. knowlesi gene has three introns at the 3′ end of the gene [Adams et al., unpublished data]. There were opening reading frames 3′ to the stop codon of P. vivax that were homologous to the three exons at the 3′ end in the P. knowlesi gene. The introns of P. vivax were therefore defined by comparison of the amino acid sequence of exons of P. knowlesi to homologous regions in P. vivax and by the consensus splice sequences for malaria and other eukaryotic genes (GTA at the 5′ end and YAG at the 3′ end) [Weber, J. L., Exp. Parasitol. 66, 143-170 (1988) and Mount, S. M., Nucleic Acids Res. 10, 459-472 (1981)). The three intron sequences so delineated are highly homologous to the P. knowlesi introns (FIG. 14). Thus, the evidence for the existence of three introns in P. vivax is based on homology of the 3′ exons and homology of the three introns between *P. vivax* and *P. knowlesi*. Because mRNA of *P. vivax* was not available, the presence of introns in *P. vivax* could not be confirmed at this time.

The complete DNA sequence and structure of *P. vivax* Duffy receptor gene are shown in FIGS. 12 and 15. The deduced amino acid sequence encoded by *P. vivax* Duffy receptor gene predicts a polypeptide of 1115 amino acids that contains a 22 amino acid putative signal sequence at the amino-terminus, a 18 amino acids transmembrane region followed by 45 amino acids at the carboxyl-terminus. There was no significant similarity to any proteins in the Swiss-prot 13 database (Intelligenetics).

Comparison of the predicted amino acid sequence between *P. vivax* and *P. knowlesi* reveals striking conservation of several major features (FIGS. 12, 15 and 16). In the sequence amino to the transmembrane region, two areas of high homology are separated by a middle, nonhomologous region (275 amino acids in *P. vivax* and 242 amino acids in *P. knowlesi*). 65.4% of the amino acids in *P. vivax* are identical in *P. knowlesi* gene in the amino homologous region and 61.0% in the carboxyl homologous region. A repeat pentamer sequence in *P. knowlesi*, not present in *P. vivax*, separates the carboxyl homologous region. Both proteins are cysteine-rich in these two homologous regions (3.5% in the amino and 5.9% in the carboxyl homologous region, respectively). All of the cysteines are positionally conserved (FIG. 12). The middle, nonhomologous region is proline-rich and cysteine-free in both *P. vivax* and *P. knowlesi* (FIGS. 16A and 16B); however, the positions of the prolines are not conserved in the nonhomologous region. This nonhomologous region is relatively poor in aromatic residues when compared to the homologous regions (FIG. 16C), which partially explains the hydrophilicity of this region (FIG. 17).

Since there are two or three homologous genes in the Duffy receptor family of *P. knowlesi*, it was important to determine whether the nonhomologous region of *P. vivax* would hybridize to any one of the other two possible *P. knowlesi* genes. The nonhomologous region of *P. vivax* which was synthesized by PCR was used as a probe to hybridize to *P. knowlesi* genomic DNA. None of the three EcoRI fragments of 4 kb, 6 kb, and 10 kb hybridized to the nonhomologous region of *P. vivax*, indicating that the 10 kb and 4 kb genomic EcoRI fragments of *P. knowlesi* are also nonhomologous in the middle region to the *P. vivax* gene.

In order to determine if there was also a family of genes in *P. vivax*, pPvDR was hybridized with restriction digests of genomic DNA (FIG. 13B). Two bands were observed on HindIII digestion: a major band at 4.1 kb and a faint, diffuse band at >20 kb. The upper one was in the area of the gel where the restricted DNA began to run and may have been incompletely digested DNA. The DraI digest had a single band of strong intensity at 2.7 kb, a diffuse band of weak intensity at around 4.4 kb (which is probably nonspecific hybridization) and a series of bands at around 150 to 300 bp. Except for the weak 4.4 kb band these sizes were consistent with the predicted restriction sites within pPvDR (2683 bp, 152 bp, 199 bp, 211 bp, 314 bp, 319 bp) A PCR fragment from the last 3′ DraI site to the 3′ HindIII site of pPvDR hybridized to a small fragment at around 300 bp, but not to the weak 4.4 kb band of *P. vivax*, suggesting that the 4.4 kb fragment may result from nonspecific binding. The EcoRI digest gave two fragments. As there was an EcoRI site within pPvDR, the inventors probed separately with the 2.7 and 1.4 kb HindIII/EcoRI fragments from pPvDR (FIGS. 13C and 13D). The 2.7 kb fragment hybridized with the 3.8 kb EcoRI fragment and not the 2.3 kb fragment of *P. vivax* genomic DNA. The 1.4 kb fragment only hybridized with the 2.3 kb genomic fragment. The data of the EcoRI digest were consistent with a single copy in *P. vivax* whereas in *P. knowlesi* there was hybridization with three chromosomes and expression of at least two Duffy receptor family genes.

The fact that the antisera to fusion proteins and a peptide derived from sequences within the cloned *P. knowlesi* gene immunoprecipitated rhesus erythrocyte binding proteins, two of which are definitely Duffy binding proteins, indicate that the gene encodes a member of the *P. knowlesi* Duffy receptor family or a highly homologous gene from a gene family has been cloned. Expression of a *P. knowlesi* Duffy receptor gene family is indicated by the following data: 1) three homologous regions in the genome on three different chromosomes; 2) two transcripts observed on Northern blots; 3) three products from in vitro translation of late schizont mRNA immunoprecipitated by anti-Duffy receptor antisera; 4) hybrid arrest of these three in vitro translation products by antisense DNA from the sequence of the cloned gene; and 5) three membrane-bound proteins of merozoites immunopreciptated by anti-Duffy receptor antisera. The analogous gene from *P. vivax* hybridizes with a single locus in the *P. vivax* genome, indicating that it is the Duffy receptor. The important structural amino acids, the location and sequence of these introns in *P. vivax* are highly homologous to the *P. knowlesi* gene. The cysteines in homologous region are conserved in number and position which would fold the two proteins in a similar manner.

Thus, the evidence from homology to a single copy gene in *P. vivax* and the inhibition of in vitro translation of the major immunoprecipitated transcript indicate that a member of the *P. knowlesi* Duffy receptor family has been cloned.

All publications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. In selected DNA segment encoding a Duffy receptor of a Plasmodium knowlesi or Plasmodium vivax parasite having an amino acid sequence as defined in FIG. 7 or FIG. 12.

2. The DNA segment according to claim 1 wherein said parasite is Plasmodium knowlesi.

3. The DNA segment according to claim 1 wherein said parasite is Plasmodium vivax.

4. A recombinant DNA molecule comprising:
   i) said DNA segment according to claim 1; and
   ii) a vector.

5. A host cell comprising the recombinant DNA molecule according to claim 4, which expresses said protein encoded in said recombinant DNA molecule.

6. The host cell according to claim 5 which is Escherichia coli, or staphylococcus.

7. The host cell according to claim 5 which is eukaryotic cell.

8. A method of producing a recombinant Duffy receptor comprising culturing said host cell according to claim 5, in a manner allowing expression of said receptor and isolation of said receptor.

9. An isolated DNA segment including a peptide of at least 5 amino acids of a Duffy receptor of a Plasmodium knowlesi or Plasmodium vivax parasite as defined in FIG. 1 or FIG. 8.

10. The DNA segment according to claim 1 having at least 15 contiguous nucleotides of the sequence defined in FIG. 1 or FIG. 9.

* * * * *

UNITED STATES PATENT AND TRADEMARK OFFICE
CERTIFICATE OF CORRECTION

PATENT NO. : 5,198,347
DATED : Mar. 30, 1993
INVENTOR(S) : Miller et al.

It is certified that error appears in the above-identified patent and that said Letters Patent is hereby corrected as shown below:

In column 20, claim 1, line 1, delete "In selected" and substitute therefor, --An isolated--;

In column 20, claim 1, line 4, delete "FIG. 7" and substitute therefor, --FIG. 1--;

In column 20, claim 7, line 1, delete "which is eukary-" and substitute therefor, --which is a eukary- --;

In column 21, claim 9, line 1, delete "including" and subsitute therefor, --encoding--;

In column 22, line 2, delete "FIG. 8" and substitute therefor, --FIG. 12--; and

In column 22, claim 10, line 3, delete "FIG. 9" and substitute --FIG. 12--.

Signed and Sealed this

Twenty-second Day of February, 1994

Attest:

BRUCE LEHMAN

*Attesting Officer*   *Commissioner of Patents and Trademarks*